(12) United States Patent
Curran et al.

(10) Patent No.: US 6,723,853 B2
(45) Date of Patent: Apr. 20, 2004

(54) INTERMEDIATES AND METHODS OF PREPARATION OF INTERMEDIATES IN THE ENANTIOMERIC SYNTHESIS OF (20R) HOMOCAMPTOTHECINS AND THE ENANTIOMERIC SYNTHESIS OF (20R) HOMOCAMPTOTHECINS

(75) Inventors: Dennis P. Curran, Pittsburgh, PA (US); Ana E. Gabarda, Boston, MA (US)

(73) Assignee: University of Pittsburgh, Pittsburgh, PA (US)

( * ) Notice: Subject to any disclaimer, the term of this patent is extended or adjusted under 35 U.S.C. 154(b) by 0 days.

(21) Appl. No.: 09/940,059

(22) Filed: Aug. 27, 2001

(65) Prior Publication Data

US 2003/0073840 A1 Apr. 17, 2003

(51) Int. Cl.[7] .................... C07D 491/14; C07D 491/22; A61K 31/47
(52) U.S. Cl. ...................... 546/294; 546/295; 546/301; 514/280; 514/283
(58) Field of Search ................. 546/295, 294, 546/301; 514/280, 283

(56) References Cited

U.S. PATENT DOCUMENTS 5,468,859 A  11/1995  Fortunak (List continued on next page.)

FOREIGN PATENT DOCUMENTS

US  PCT/US02/26426  8/2002

(List continued on next page.)

OTHER PUBLICATIONS

Curran, D.P. and Liu, H., "New 4+1 Radical Annulations—A Formal Total Synthesis of (+/−)–Camptothecin," J. Am. Chem Soc., 114, 5863–5864 (1992). Published Jul. 1, 1992.

(List continued on next page.)

*Primary Examiner*—Ceila Chang
*Assistant Examiner*—Janet L Coppins
(74) *Attorney, Agent, or Firm*—Bartony & Hare, LLP

(57) ABSTRACT

A method of synthesizing a compound having the formula:

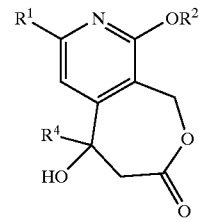

from a compound having the formula:

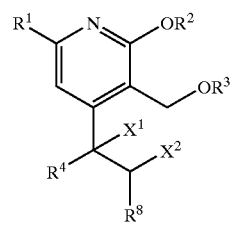

wherein $R^1$ is hydrogen, fluorine, chlorine or $SiR^5R^6R^7$, wherein $R^5$, $R^6$, and $R^7$ are independently the same or different an alkyl group or an aryl group, $R^2$ is an alkyl group, $R^3$ is a protecting group, $R^4$ is an alkyl group, an allyl group, a propargyl group —$CO_2H$, or a benzyl group, $R^8$ is —$CO_2R^{10}$, wherein $R^{10}$ is an alkyl group or an aryl group, $X^1$ is OH and $X^2$ is H, includes the step of exposing compound (III) to at least one of an organic acid or an inorganic acid. A compound has the general formula (III).

23 Claims, 5 Drawing Sheets

Camptothecin and Analogs (20S)-camptothecin (cpt)

(20R)-homocamptothecin (hcpt)

DB-67, a typical substituted camptothecin (silatecan)

10,11-difluorohomocamptothecin, a typical substituted homocamptothecin

U.S. PATENT DOCUMENTS

| | | | |
|---|---|---|---|
| 5,700,939 A | 12/1997 | Fortunak | |
| 5,744,605 A | 4/1998 | Curran | |
| 5,910,491 A | 6/1999 | Hausheer | |
| 5,935,967 A | 8/1999 | Hausheer | |
| 5,981,542 A | * 11/1999 | Bigg et al. | 514/283 |
| 6,057,303 A | 5/2000 | Haridas | |
| 6,136,978 A | 10/2000 | Curran | |
| 6,150,343 A | 11/2000 | Curran | |
| 6,207,832 B1 | 3/2001 | Curran | |
| 6,211,371 B1 | 4/2001 | Curran | |
| 6,252,079 B1 | 6/2001 | Curran | |
| 6,372,906 B1 | 4/2002 | Curran | |

FOREIGN PATENT DOCUMENTS

| | | |
|---|---|---|
| WO | WO 96/31513 | 10/1996 |
| WO | WO97/00876 | 1/1997 |
| WO | WO98/07727 | 2/1998 |
| WO | WO98/28305 | 7/1998 |
| WO | WO98/35940 | 8/1998 |
| WO | WO99/11646 | 3/1999 |
| WO | WO 00/50427 | 8/2000 |
| WO | WO 00/61146 | 10/2000 |

OTHER PUBLICATIONS

Curran, D.P., "The Camptothecins—A reborn Family of Antitumor Agents", J. Chin. Chem. Soc., 40, 1–6 (1993). Published Feb. 1993.

Curran, D.P. et al., "Recent Applications of Radical Reactions in Natural Product Synthesis," Pure Appl. Chem., 65, 1153–1159 (1993). Published Jun. 1993.

Curran, D.P. et al., "Cascade Radical Reactions of Isonitriles: A Second–Generation Synthesis of (20S)–Camptothecin, Topotecan, Irinotecan, and Gl–147211C," Angew. Chem. Int. Ed, 34, 2683–2684 (1995). Published Jan. 5, 1996.

Curran, D.P., Liu, H.; Josien, H; Ko, S.B., "Tandem Radical Reactions of Isonitriles with 2–pyrdonyl and other aryl radicals: Scope and Limitations, and a First Generation Sunthesis of (+/–)–Camptothecin," Tetrahedron, 52, 11385–11404 (1996). Published Aug. 1996.

Josien, H. et al., "Synthesis of (S)–mappicine and Mappicine Ketone Via Radical Cascade Reaction of Isonitirles," Tetrahedron, 53, 8881–8886 (1997). Published Jun. 30, 1997.

Josien, H. et al., "7–Silycamptothecins (Silatecans): A New Family of Camptothecin Antitumor Agents," Bioorg. Med. Chem. Lett. 7, 3189–3295 (1997).

Josien, H. et al., "A General Synthetic Approach to the (20S)–Camptothecin Family of Antitumor Agents by a Regiocontrolled Cascade Radical Cyclization of Aryl Isonitriles," Chem. Eur. J. 4, 67–83 (1998). Published Jan. 1998.

Zihou, M. et al., "Reduced Albumin Binding Promotes the Stability and Activity of Topotecan in Human Blood," Biochemistry, 34, 13722–13727 (1995).

Burke, T.G. and Zihou, M., "The Structural Basis of Camptothecin Interaction with Human Serum Albumin: Impact on Drug Stability," J. Med. Chemistry, 37, 40–46 (1994).

Zihou, M. and Burke, T.G., "Marked Interspecies Variations Concerning the Interactions of Camptothecin with Serum Albumins: A Frequency–Domain fluorescence Spectroscopic Study," Biochemistry, 33, 12540–12545 (1994).

Zihou, M. and Burke, T.G., "Differential Interactions of Camptothecin Lactone and Carboxylate Forms with Human Blood Components," Biochemistry, 33, 10325–10336 (1994).

Burke, T.G., and Zihou, M., "Ethyl Substitution at the 7 Position Extends the Half–Life of 10–Hydroxycamptothecin in the Presence of Human Serum Albumin," J. Med. Chemistry, 37:17, 2580–2582 (1993).

Burke, T.G. et al., "Lipid Bilayer Partitioning and Stability of Camptothecin Drugs," Biochemistry, 32:20, 5352–5364 (1993).

Zihou, M. and Burke, T.G., Preferential Binding of the Carboxylate Form of Camptothecin by Human Serum Albumin, Anal. Biochem., 212, 285–287 (1993).

Mura, Akihiro, et al., "Enantioselective Synthesis of 20(S)–Camptothecin Using an Enzyme–Catalyzed Resolution", Tetrahedron: Asymmetry, Elsevier Science Publishers, Amsterdam, NL, vol. 9, No. 13, Jul. 3, 2285–2291 (1998).

Burke, T.G. and Tritton, T.R., "Location and Dynamics of Anthracycline Bound to Unilamellar Phosphatidylcholine Vesicles," Biochemistry, 24, 5972–5980 (1985).

Burke, T.G. and Tritton, T.R., "Structural Basis of Anthracycline Selectivity for Unilamellar Phosphatidylcholine Vesicles: An Equilibrium Binding Study," Biochemistry, 24, 1768–1776 (1985).

Lavergne, O., et al., J. Med. Chem., 41, 5410–5419 (1998).

Lavergne, O., et al., Bioorg. Med. Chem. Lett., 7, 2235–2238 (1997).

Jew, Sang–Sup, et. al., "Enantioselective Synthesis of 20 (S)–Camptothecin Using Sharpless Catalytic Asymmetric Dihydroxylation", Tetrahedron: Asymmetry, Elsevier Science Publishers, Amsterdam, NL, vol. 6, No. 6, 1245–1248 (Jun. 1, 1995).

Yabu, Kazuo et. al., "Switching Enantiofacial Selectivities Using One Chiral Source: Catalytic Enantioselective Systhesis of the Key Intermediate for (20S)–Camptothecin Family by (S)–Selective Cyanosilylation of Ketones", Journal of the American Chemical Society, 123, 9908–9909 (2001).

Du, Wu, et. al., "Synthesis and Evaluation of a Novel E–Ring Modified alpha–Hydroxy Keto Ether Analogue of Camptothecin", Bioorganic & Medicinal Chemistry 10 103–110 (2002).

Linker, T., Angew, Chem., Int. Ed. Engl., 36, 2060 (1997).

Han, X., et al., J. Am. Chem. Soc.121(33); 7600–7605 (1999).

Pollack, I. F.; et al., Cancer Research, 59, 4898 (1999).

Bom, D., et al., J. Med. Chem., 42, 3018 (1999).

Curran, D. P. and Ko, S. B., J. Org. Chem., 59, 6139–6141 (1994).

\* cited by examiner

Figure 1. Camptothecin and Analogs
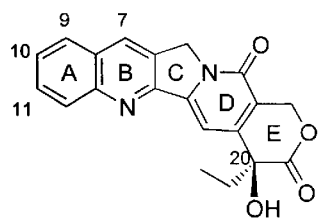
(20S)-camptothecin (cpt)
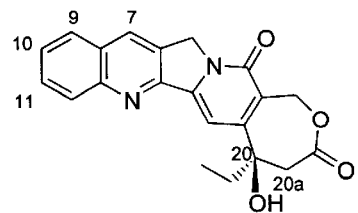
(20R)-homocamptothecin (hcpt)
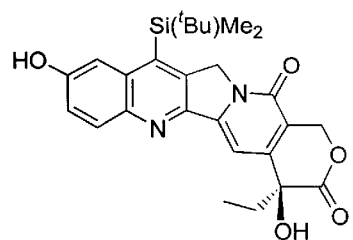
DB-67, a typical substituted
camptothecin (silatecan)
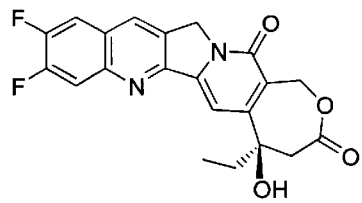
10,11-difluorohomocamptothecin, a typical substituted
homocamptothecin Figure 2a. Synthesis of (20R)-Homocamptothecins by a Cascade Radical Annulation
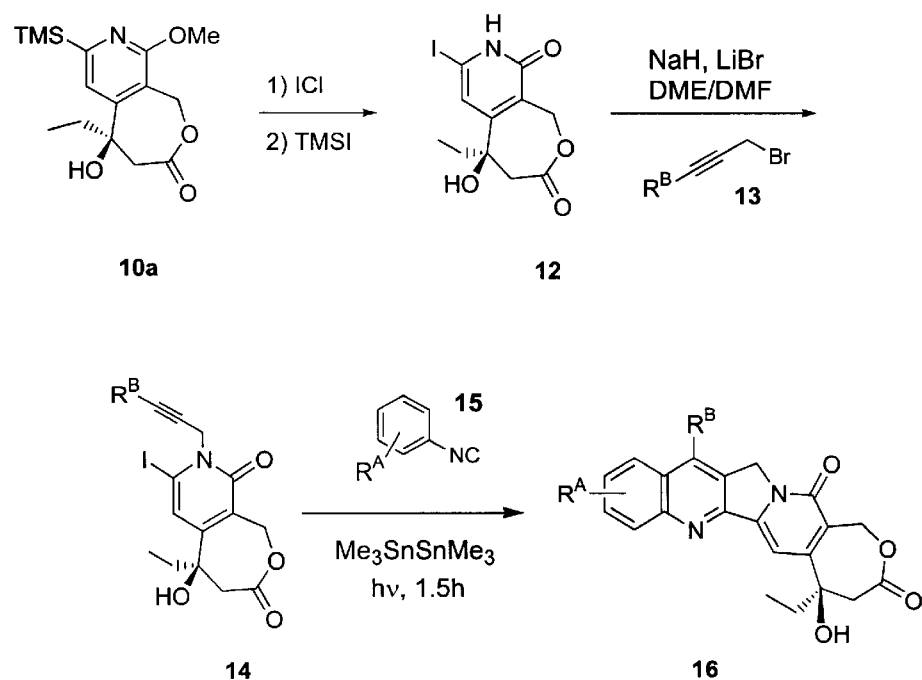
Figure 2b. French Route to the Homocamptotecin Drug Candidate
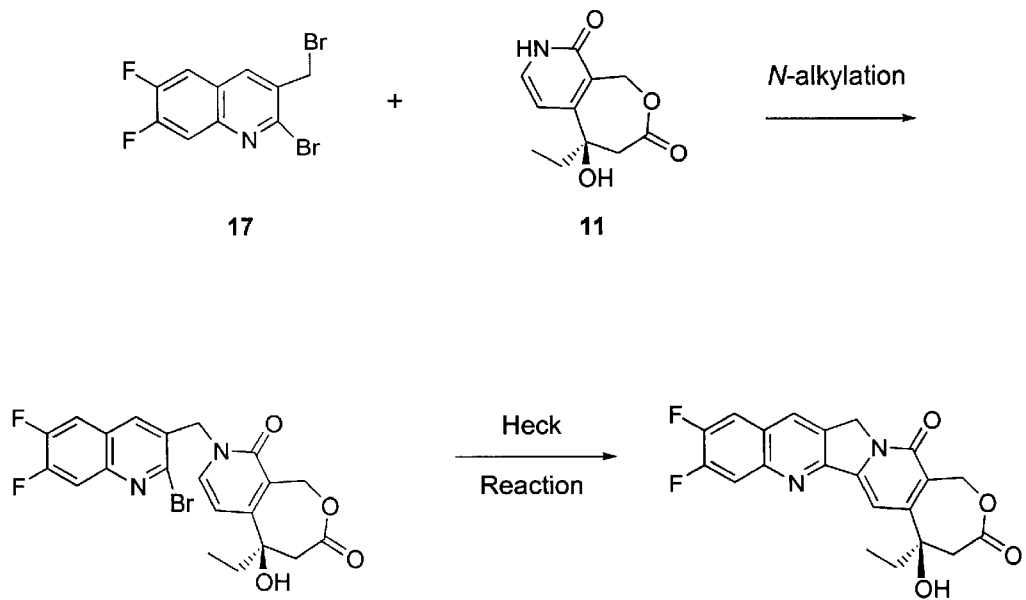

Figure 3. Enantioselective Synthesis of Lactone Pyridones 11 and 12.

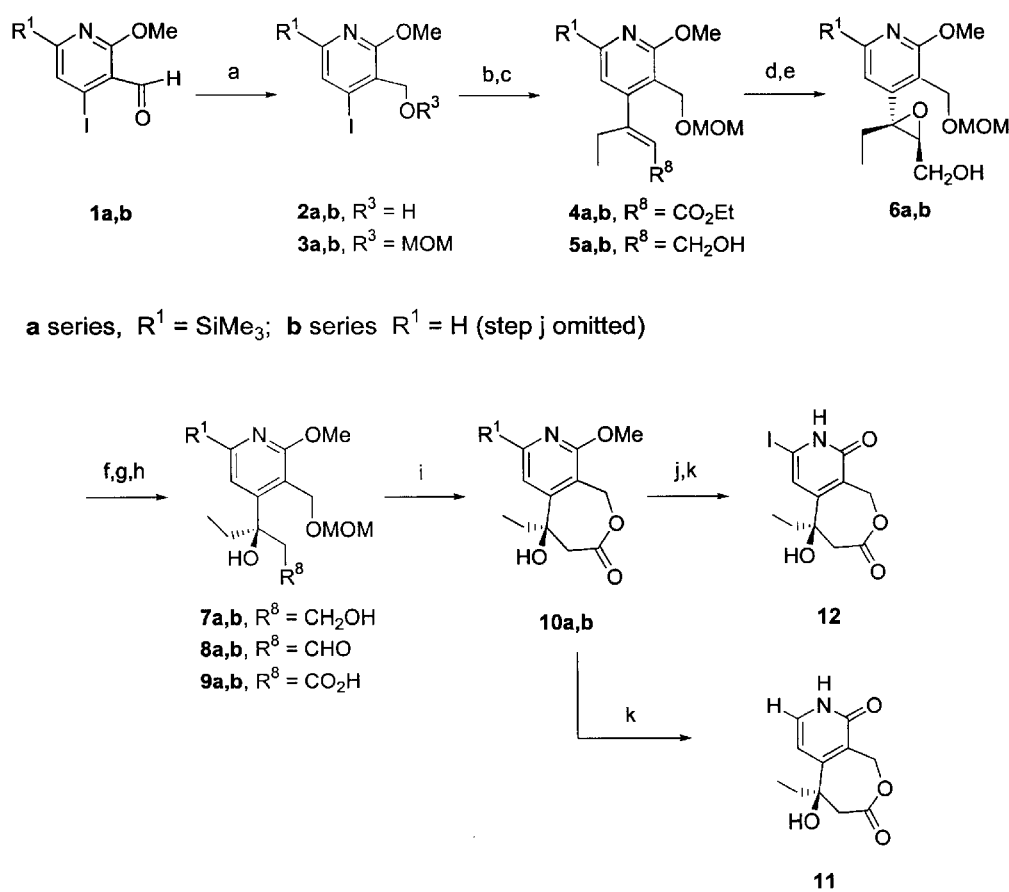

(a) NaBH$_4$, EtOH, -40 °C, 1h, 78%; (b) MOMCl, $^i$Pr$_2$EtN, CH$_2$Cl$_2$, 0 °C to rt, 88%; (c) (E)-Bu$_3$SnEtC=CHCO$_2$Et, Pd(PPh$_3$)$_4$, LiCl, CuCl, DMSO, 60 °C, 17h, 80%; (d) LAH, Et$_2$O, 0 °C to rt, 90%; (e) Ti(O$^i$Pr)$_4$, $^t$BuOOH, -20 °C, 60h, 79%, 90%ee; (f) LAH, Et$_2$O, 0 °C to rt, 100%; (g) Dess-Martin periodinane, CH$_2$Cl$_2$, rt, 3h, 80%; (h) NaClO$_2$, NaH$_2$PO$_4$, 2-methyl-2-butene, $^t$BuOH/H$_2$O, rt, 16h, 100%; (i) TFA, rt, 24h, 70%; (j) ICl, 0 °C to rt, CH$_2$Cl$_2$/CCl$_4$, 38% (86% based upon recovered SM); (k) TMSCl, NaI, 0.6 eq H$_2$O, MeCN, 65 °C, 5h, 61%

Figure 4. A Representative Variant of the Route in Figure 3.
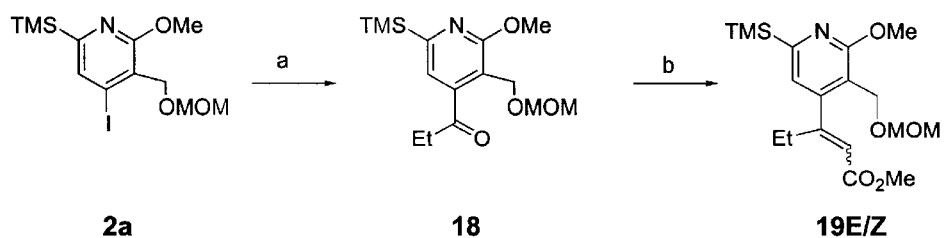
a) $^i$PrMgCl; CuCN, LiCl; CH$_3$CH$_2$COCl, –40°C, THF, 69%; b) (MeO)$_2$P(O)CH$_2$CO$_2$Me, KO$^t$Bu, THF, 0°C, E-isomer, 27%, Z-isomer 43%.

Figure 5. Illustrative Example of the Process to Increase the Enantiopurity of beta Hydroxy Lactones
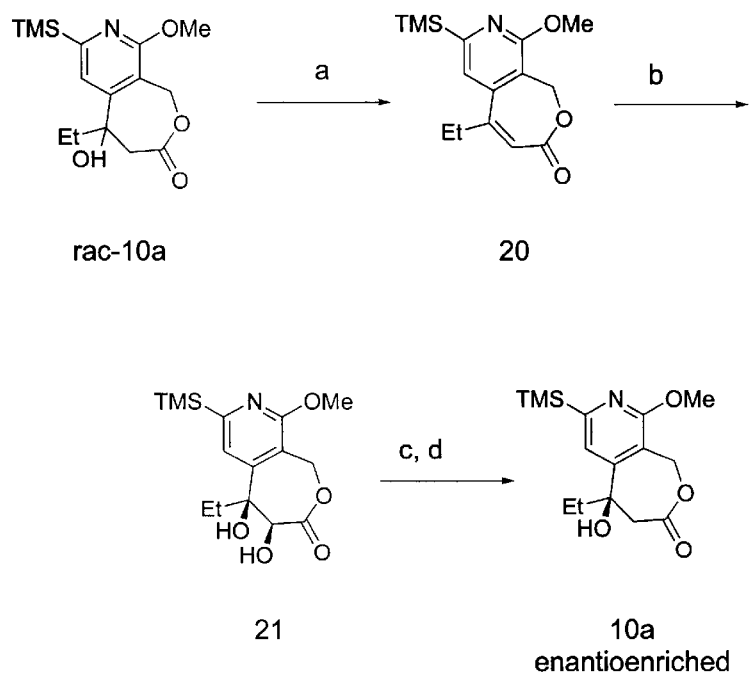
a) Burgess reagent, rt, THF, 12 h; b) potassium ferricyanide, potassium carbonate, methanesulfonamide, (DHQD)$_2$-PYR, OsO$_4$, t-BuOH/H$_2$O, 0 °C, c) and d), activation and reduction; see, for example, Curran, D. P.; Ko, S. B. *J. Org. Chem.* 1994, *59*, 6139.

INTERMEDIATES AND METHODS OF PREPARATION OF INTERMEDIATES IN THE ENANTIOMERIC SYNTHESIS OF (20R) HOMOCAMPTOTHECINS AND THE ENANTIOMERIC SYNTHESIS OF (20R) HOMOCAMPTOTHECINS

GOVERNMENT INTEREST

This invention was made with government support under grant RO1 GM33372 awarded by the National Institutes of Health. The government has certain rights in this invention.

BACKGROUND OF THE INVENTION

The present invention relates to methods of preparation of homocamptothecins and intermediates therefor and, particularly, to methods and intermediates for the enantioselective synthesis (20R)-homocamptothecins.

References set forth herein may facilitate understanding of the present invention or the background of the present invention. Inclusion of a reference herein, however, is not intended to and does not constitute an admission that the reference is available as prior art with respect to the present invention.

In general, camptothecins and homocamptothecins as illustrated in FIG. 1 (sometimes referred to generally herein as camptothecins or the camptothecin family) are DNA topoisomerase I inhibitors useful, for example, as anticancer drugs. Analogs of the natural product camptothecin frequently have one or more substituents in place of hydrogen in the A and/or B rings at carbons 7, 9, 10, and/or 11. These analogs are among the most important classes of compounds available for treatment of solid tumors. Topotecan (tpt) and CPT-11 were the first two members in the camptothecin family to gain United States Food and Drug Administration full approval status (topotecan in 1996 as second-line therapy for advanced epithelial ovarian cancer, topotecan again in 1998 for the treatment of small cell lung cancer, CPT-11 in 1998 as first-line therapy for colon cancer).

Recently, Lavergne et al. have shown that expansion of the E-ring of camptothecin to produce a homocamptothecin (hcpt) enhances the solution stability of camptothecin while maintaining anticancer activity. U.S. Pat. No. 5,981,542; PCT International Patent Application No. PCT/FR00/00461; Lavergne, O., et al., *J. Med. Chem.*, 41, 5410–5419 (1998); and Lavergne, O., et al., *Bioorg. Med. Chem. Lett.*, 7, 2235–2238 (1997). Once again, many of the most important compounds in this class have one or more substituents on rings A and/or B. For example, 10,11-difluorohomocamptothecin is in early stage clinical trials.

7-Silyl camptothecins and 7-silyl homocamptothecins (sometimes referred to as silatecans and homosilatecans) are important classes of lipophilic camptothecin and homocamptothecin analogs, See, for example, a) Josien, H., et al., *Bioorg. Med. Chem. Lett.*, 7, 3189 (1997); b) Pollack, I. F.; et al., *Cancer Research*, 59, 4898 (1999); Bom, D., et al., *Clinical Cancer Research*, 5, 560 (1999); Bom, D., et al., *J. Med. Chem.*, 42, 3018 (1999).

Many of the most interesting silatecans and homosilatecans contain one or more additional substituents (for example, hydroxy or amino) in the A ring, and the combination of these substituents can provide significant improvements over either of the corresponding mono-substituted analogs. For example, DB-67, or 7-tert-butyldimethylsilyl-10-hydroxycamptothecin, is highly active against cancer cells and tumors and possesses many favorable physical and pharmacological properties. Silatecans and homosilatecans in general show a number of attractive features including high activity against a broad spectrum of solid tumors, low binding to blood proteins, resistance to lactone opening, high lipophilicity, and potential oral availability among others.

Camptothecins, silatecans, homocamptothecins and homosilatecans (referred to herein generally as "camptothecins" and "homocamptothecins") have been prepared using cascade radical annulation routes. See, for example, U.S. Pat. Nos. 6,136,978, 6,150,343, 6,207,832 and 6,211,371, Curran, D. P., et al., *Angew. Chem., Int. Ed. Eng.*, 34, 2683 (1995) and Josien, H., et al., *Chem. Eur. J.*, 4, 67 (1998). Those total synthetic routes are highly flexible and allow the preparation of a diverse array of, for example, silatecan and homosilatecan analogs by both traditional and parallel routes. In that regard, substantially any substituent can be placed on, for example, the A- or B-ring of the camptothecin structure using those synthetic routes.

The cascade radical annulation route to homocamptothecins and homosilatecans is summarized in FIG. 2a. The key iodopyridone 12 is first N-propargylated with a propargyl bromide 13 and the resulting intermediate 14 is next reacted with an aryl isonitrile 15 under the conditions of cascade radical annulation. The substituent on the propargyl bromide ($R^B$) becomes the B-ring substituent at C7 while the substituent(s) on the isonitrile ($R^A$) become(s) the A-ring substituents. In this way, many different homocamptothecins and homosilatecans 16 can be made from a single key intermediate 12. In turn, 12 is made from 10a by the steps of iododesilylation and demethylation.

In the Lavergne route to homocamptothecins (FIG. 2b), compound 11 is alkylated with a bromomethyl quinoline 17 followed by Heck type cyclization. Accordingly, compounds of the structures 10–12 and their relatives are crucial intermediates in the synthesis of homocamptothecins, homosilatecans, and analogs.

Unfortunately, current syntheses of compounds 10–12 are racemic synthesis, requiring subsequent resolution of the active enantiomer. These resolutions add extra steps and are wasteful because the undesired enantiomer (50% of the mixture) must be discarded.

It is thus very desirable to develop enantioselective synthetic routes and intermediate compounds for use therein for the synthesis of biologically active (20R)-homocamptothecins.

SUMMARY OF THE INVENTION

In one aspect, the present invention provides generally methods of synthesis of compounds of the formula:

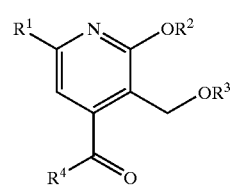

I from readily available compounds of the formula (IV):

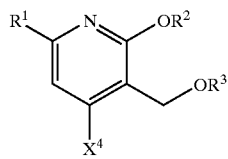

IV wherein $R^1$ is, for example, hydrogen, fluorine, chlorine or $SiR^5R^6R^7$ wherein $R^5$, $R^6$, and $R^7$ are independently the same or different an alkyl group (preferably a lower alkyl group) or an aryl group. $R^2$ is an alkyl group (preferably, a lower alkyl group). $R^3$ is a protecting group (for example, acetate, methoxymethyl or tert-butyldimethylsilyl). $R^4$ is an alkyl group (preferably, a lower alkyl group), an allyl group, a propargyl group or a benzyl group. $X^4$ is H, Cl, Br or I.

Preferred embodiments of the compound of formula (I) for use in the synthetic methods of the present invention include those in which $R^1$ is H or a trimethylsilyl group, $R^2$ is a lower alkyl group, $R^3$ is a methoxymethyl group, and $R^4$ is an ethyl group.

In one embodiment, a nucleophilic organometallic species of the formula (IVa):

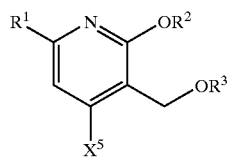

IVa is produced by converting $X^4$ of the compound of formula (IV) to a metal or a metal-containing group $X^5$ (referred to herein collectively as a "metal-containing group"—for example Li, CuCN, MgBr or MgI). The nucleophilic organometallic species is generated either by deprotonation (in the case that $X^4$ is H) or halogen metal exchange (in the case that $X^4$ is Cl, Br or I). If desirable, the initial metal-containing group can be exchanged for another by transmetallation. Preferred metals for metalation or transmetalation to generate nucleophiles have a Pauling electronegativity less than or equal to about 1.9, and more preferred metals have a Pauling electronegativity less than or equal to about 1.6. Examples of preferred metals include lithium, sodium, potassium, cesium, magnesium, titanium, chromium, zirconium, copper, and aluminum. Even more preferred metals are lithium, magnesium and copper.

The resultant nucleophilic species is reacted with a suitable electrophile to effect direct or indirect acylation to the compound of formula (I). One example of a direct acylation is the reaction of the nucleophile with an acid chloride $R^4C(O)Cl$ or with a so-called "Weinreb" amide having the formula $R^4C(O)N(Me)OMe$. An example of an indirect acylation is the reaction of the nucleophile with an aldehyde having the formula $R^4CHO$ to effect hydroxyalkylation. The resultant alcohol is then oxidized to the compound of formula (I). Many methods for acylation of nucleophiles suitable for use in the present invention are known to those skilled in the art.

In another embodiment, the Stille coupling reaction is used to effect reaction of the compound of formula (IV) wherein $X^4$ is Cl, Br or I with a compound having the formula $R^4C(O)SnR^5R^6R^7$, wherein $R^5$, $R^6$ and $R^7$ are as defined above. Preferably, $R^5$, $R^6$ and $R^7$ are independently the same or different a methyl group or a butyl group. The Stille coupling is often effected in the presence of a palladium catalyst with a ligand such as a triarylphosphine or triarylarsine. Many variants of the Stille procedure as known to those skilled in the art are suitable for use in the present invention.

In another aspect, the present invention also provides generally methods of synthesis of compounds of the formula:

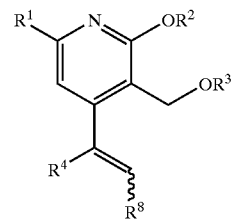

II from compounds of the formula (I) by Wittig reaction, Peterson olefination, or one of the many others methods used by those skilled in the art for the conversion of ketones into alkenes. In the compounds of formula (II), $R^1$, $R^2$, $R^3$, and $R^4$ are as defined above, and $R^8$ is —CHO, —CH$_2$OH, —CH$_2$OR$^9$, wherein $R^9$ is a protecting group, —CO$_2$H, or —CO$_2$R$^{10}$ wherein $R^{10}$ is an alkyl group (preferably a lower alkyl group) or an aryl group.

Preferred embodiments of the compound of formula (II) for use in the synthetic methods of the present invention include those in which $R^1$ is H or a trimethylsilyl group, $R^2$ is a lower alkyl group, $R^3$ is a methoxymethyl group, $R^4$ is an ethyl group, and $R^8$ is CH$_2$OH, CHO, CO$_2$Me or CO$_2$Et.

In another aspect, the present invention provides a method for direct conversion of the compounds of formula (IV) to the compounds of formula (II). In general, the compounds of formula (IV), wherein X is Cl, Br or I, are reacted under Stille reaction conditions as discussed above with compounds having the formula $R^4(R^7R^6R^5)SnC=CHR^8$.

In a further aspect, the present invention provides a method for conversion of compounds of formula (II) to compounds of the formula:

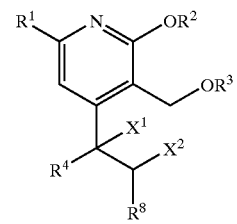

III via asymmetric hydroxylation or asymmetric epoxidation. In the compounds of formula (III), $R^1$, $R^2$, $R^3$, $R^4$ and $R^8$ are as defined above. In the compounds of formula (III), $X^1$ is OH, $X^2$ is H or OH, or together $X^1$ and $X^2$ are O (that is, an oxirane or epoxide). These compounds can further be converted to compound in which together $X^1$ and $X^2$ are OS(O)O (that is, a cyclic sulfite) or OS(O$_2$)O (that is, a cyclic sulfate) as described below.

Preferred embodiments of the compound of formula (III) for use in the synthetic methods of the present invention include those in which $R^1$ is H or a trimethylsilyl group, $R^2$ is a lower alkyl group, $R^3$ is a methoxymethyl group, $R^4$ is an ethyl group, $R^8$ is CH$_2$OH, CHO, CO$_2$H, CO$_2$R$^{10}$, wherein $R^{10}$ is as described above, $X^1$ is OH, $X^2$ is H, or $X^1$ and $X^2$ together are O.

Preferred methods of asymmetric epoxidation provide compounds of formula (III) wherein $X^1$ and $X^2$ together are O (epoxide or oxirane) and include the Sharpless asymmetric epoxidation, the Jacobsen asymmetric epoxidation or the Jacobsen-Katsuki asymmetric epoxidation. An example of a preferred method of asymmetric epoxidation is the Sharpless asymmetric epoxidation wherein $R^8$ is (E)—$CH_2OH$.

Asymmetric dihydroxylation provides compounds of formula (III) wherein $X^1$ and $X^2$ are OH. A preferred method of asymmetric dihydroxylation is the Sharpless asymmetric dihydroxylation (AD). Diols $X^1$ and $X^2$ are readily converted to cyclic sulfites ($X^1$ and $X^2$ together are OS(O)O) by standard sulfinylation reagents, for example $SOCl_2$, and to cyclic sufates ($X^1$ and $X^2$ are OS(O$_2$)O) by standard sulfonylating reagents, for example $SO_2Cl_2$. Compounds of formula (III) wherein $X^1$ is OH and $X^2$ is H can, for example, be made by reduction of epoxides, cyclic sulfites or cyclic sulfates wherein $R^8$ is CHO or preferably $CO_2R^{10}$ by reduction with, for example, samarium iodide. Compounds of formula (III) wherein $X^1$ is OH, $X^2$ is H and $R^8$=$CH_2OH$ can be made by reduction of epoxides, cyclic sulfites or cyclic sulfates by aluminum or boron hydrides. An example of a preferred reducing agent is lithium aluminum hydride. Compounds of formula (II) or (III) wherein $R^8$ is $CH_2OH$, CHO, or $CO_2R^{10}$ can be readily interconverted with each other by standard oxidation, reduction and functional group transformation reactions.

Other methods for selective removal of a secondary hydroxyl group of the compounds of formula (III) ($X^2$ is OH) in the presence of a tertiary hydroxy group ($X^1$ is OH) to give the compounds of formula (III) in which $X^2$ is H and $X^1$ is OH are well known to those skilled in the art. For example, in the case where $R^8$ is $CO_2R^{10}$, the secondary alcohol can be selectivly activated as a tosylate, a mesylate or a similar leaving group. The leaving can then be reductively removed with, for example, samarium diiodide. Alternatively, the leaving group can be displaced with, for example, bromide, iodide or phenyl selenide, and the so-formed product can be reduced with, for example, tributyltin hydride or tris(trimethylsilylsilicon) hydride. For an illustrative example of this later process, see Curran, D. P. and Ko, S. B., *J. Org. Chem.*, 59, 6139–6141 (1994), the disclosure of which is incorporated herein by reference.

In still a further aspect, the present invention provides a method for the conversion of the compounds of formula (III) wherein $R^1$, $R^2$ and $R^4$ are as defined above, $X^1$ is OH, $X^2$ is H and $R^8$ is $CO_2H$ or $CO_2R^{10}$ into compounds of the formula (V):

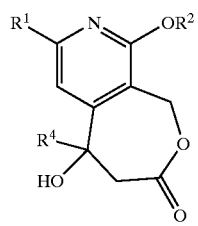

V by treatment or exposure of the compounds of formula (III) with organic or inorganic acids. Preferably, acids with a pKa of less than about 4 are used. More preferably, acids with a pKa of less than about 2 are used. An example of a preferred acid for the conversion is trifluoroacetic acid.

In a further aspect the present invention provides a method of synthesizing a compound having the formula:

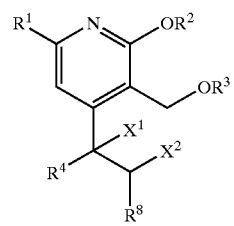

III wherein $R^1$ is hydrogen, fluorine, chlorine or $SiR^5R^6R^7$, wherein $R^5$, $R^6$, and $R^7$ are independently the same or different an alkyl group or an aryl group, $R^2$ is an alkyl group, $R^3$ is a protecting group, $R^4$ is an alkyl group, an allyl group, a propargyl group or a benzyl group, $R^8$ is —CHO, —$CH_2OH$, —$CH_2OR^9$, wherein $R^9$ is a protecting group —$CO_2H$, or —$CO_2R^{10}$, wherein $R^{10}$ is an alkyl group or an aryl group, and $X^1$ is OH, $X^2$ is H or OH, or $X^1$ and $X^2$ together are O, including the steps of:

a) converting the ketone of compound (I) to an alkene to synthesize a compound having the formula:

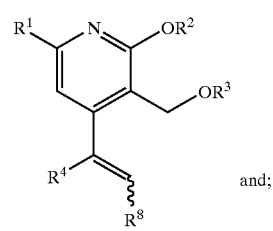

II and;

b) asymmetrically hydroxylating compound (II) or asymmetrically epoxidating compound (II).

In a further aspect, the present invention provides a method of synthesizing a compound having the formula:

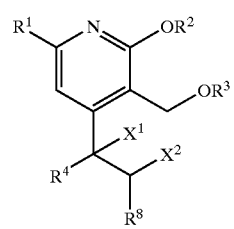

III wherein $R^1$ is hydrogen, fluorine, chlorine or $SiR^5R^6R^7$, wherein $R^5$, $R^6$, and $R^7$ are independently the same or different an alkyl group or an aryl group, $R^2$ is an alkyl group, $R^3$ is a protecting group, $R^4$ is an alkyl group, an allyl group, a propargyl group or a benzyl group, $R^8$ is —CHO, —$CH_2OH$, —$CH_2OR^9$, wherein $R^9$ is a protecting group —$CO_2H$, or —$CO_2R^{10}$, wherein $R^{10}$ is an alkyl group or an aryl group, and $X^1$ is OH, $X^2$ is H or OH, or $X^1$ and $X^2$ together are O, including the steps of:

a) reacting a compound having the formula:

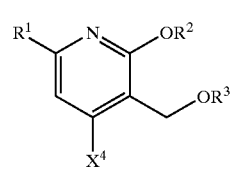

IV wherein $X^4$ is Cl, Br or I, under Stille reaction conditions with a compound having the formula $R^4(R^7R^6R^5)SnC=CHR^8$ to synthesize a compound having the formula:

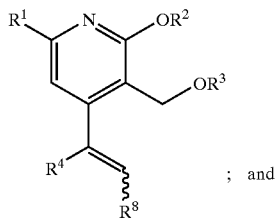

; and b) asymmetrically hydroxylating compound (II) or asymmetrically epoxidating compound (II).

In a further aspect, the present invention provides a method for increasing the enantiopurity of compounds of the general structure of formula (V). These compounds can be made as described above in enantioenriched form. The compounds of formula (V) can also be made in racemic form by the methods described in, for example, U.S. Pat. No. 5,981,542; PCT International Patent Application No. PCT/FR00/00461; U.S. Pat. Nos. 6,136,978, 6,150,343, 6,207,832 or 6,211,371, or by standard racemic applications of the asymmetric methods described herein (for example, replacement of the Sharpless asymmetric epoxidation with a standard peracid epoxidation).

Compounds of formula (V) that are racemic or of low enantiopurity (typically, 50% ee or less) are first dehydrated to compounds of formula (VI):

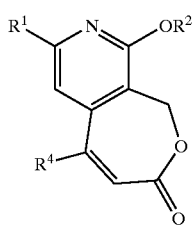

wherein $R^1$, $R^2$ and $R^4$ are as described above. A preferred dehydrating reagent is the Burgess reagent (methoxycarbonylsulfamoyltriethylammonium hydroxide). Compounds of formula (VI) can then be converted to compounds of formula (VII)

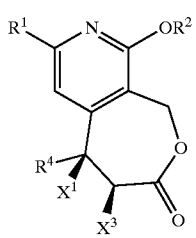

wherein $R^1$, $R^2$ and $R^4$ are as described above, and $X^1$ and $X^3$ are OH or together are O, via asymmetric dihydroxylation or asymmetric epoxidation. A preferred method for synthesis of compounds of formula (VII) wherein $X^1$ and $X^3$ are OH is the Sharpless asymmetric dihydroxylation. Compounds of formula (VII) wherein $X^1$ and $X^3$ are OH can be converted to compounds of formula (VII) wherein $X^1$ and $X^3$ are together cyclic sulfites or cyclic sulfates and from there to compounds of formula (V) by methods analogous to those described for compounds of formula (III). Compounds wherein $X^1$ and $X^3$ together are O can be converted to compounds of formula (V) by reduction with, for example, samarium dioidide.

In still another aspect, the invention provides a method for increasing the enantiopurity of a homocamptothecin (that is, homocamptothecin or a derivative of homocamptothecin bearing, for example, substituents in rings A and/or B) including the steps of a) dehydration of the C20 hydroxy group to give a C20–C20a alkene, b) Sharpless asymmetric dihydroxylation to give a C20, C20a diol, c) activation of the secondary hydroxy group on C20a, and d) reductive removal of the activated group. Step a generally follows the methods described for the compounds of formula (VI), whereas steps b through d follow the methods described for the compounds of formulas (III) and (VII).

The process of the present invention for increasing the enantiopurity of homocamptothecin has broad scope with respect to substituents on the A and B rings, and is generally applicable to the homocamptothecins (including homosilatecans) including substituents as described, for example, in U.S. Pat. No. 5,981,542; PCT International Patent Application No. PCT/FR00/00461; U.S. Pat. Nos. 6,136,978, 6,150,343, 6,207,832, 6,211,371 and/or elsewhere, whether prepared by total synthesis or semisynthesis. Those skilled in the art will recognize the protection of certain A and B ring substituents, for example hydroxyl and amino, may be needed during some or all of the steps of this method of the invention.

In another aspect, the present invention provides generally a compound having the formula (I):

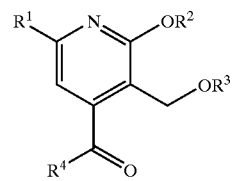

wherein $R^1$ is, for example, fluorine, chlorine or $SiR^5R^6R^7$ wherein $R^5$, $R^6$, and $R^7$ are independently the same or different an alkyl group (preferably a lower alkyl group) or an aryl group. $R^2$ is an alkyl group (preferably, a lower alkyl group). $R^3$ is a protecting group (for example, acetate, methoxymethyl or tert-butyldimethylsilyl), and wherein $R^4$ is an alkyl group (preferably, a lower alkyl group), an allyl group, a propargyl group or a benzyl group.

In another aspect, the present invention further provides a compound having the formula (II):

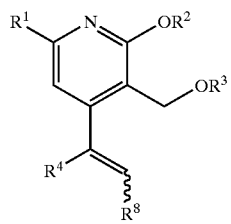

wherein $R^1$ is, for example, hydrogen, fluorine, chlorine or $SiR^5R^6R^7$ wherein $R^5$, $R^6$, and $R^7$ are independently the same or different an alkyl group (preferably a lower alkyl group) or an aryl group. $R^2$ is an alkyl group (preferably, a lower alkyl group). $R^3$ is a protecting group (for example, acetate, methoxymethyl or tert-butyldimethylsilyl). $R^4$ is an alkyl group (preferably, a lower alkyl group), an allyl group, a propargyl group or a benzyl group. $R^8$ is —CHO, —CH$_2$OH, —CH$_2$OR$^9$, wherein $R^9$ is a protecting group, —CO$_2$H, or —CO$_2$R$^{10}$ wherein $R^{10}$ is an alkyl group (preferably a lower alkyl group) or an aryl group. The alkene can have either the E or the Z geometry in compound of formula (II).

In a further aspect, the present invention provides a compound having the formula (III):

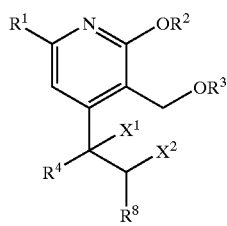

III wherein $R^1$ is fluorine, chlorine or SiR$^5$R$^6$R$^7$, wherein $R^5$, $R^6$, and $R^7$ are independently the same or different an alkyl group or an aryl group, $R^2$ is an alkyl group, $R^3$ is a protecting group, $R^4$ is an alkyl group, an allyl group, a propargyl group or a benzyl group, $R^8$ is —CHO, —CH$_2$OH, —CH$_2$OR$^9$, wherein $R^9$ is a protecting group —CO$_2$H, or —CO$_2$R$^{10}$, wherein $R^{10}$ is an alkyl group or an aryl group, and $X^1$ is OH, $X^2$ is H or OH, or $X^1$ and $X^2$ together are O, OS(O)O or OS(O$_2$)O.

In another aspect, the present invention provides a compound having the formula (III):

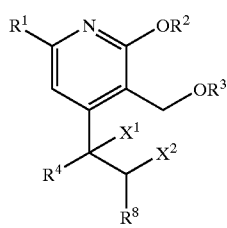

III $R^1$ is hydrogen, fluorine, chlorine or SiR$^5$R$^6$R$^7$, wherein $R^5$, $R^6$, and $R^7$ are independently the same or different an alkyl group or an aryl group, $R^2$ is an alkyl group, $R^3$ is a protecting group, $R^4$ is an alkyl group, an allyl group, a propargyl group or a benzyl group, $R^8$ is —CHO, —CH$_2$OH, —CH$_2$OR$^9$, wherein $R^9$ is a protecting group —CO$_2$H, or —CO$_2$R$^{10}$, wherein $R^{10}$ is an alkyl group or an aryl group, and $X^1$ is OH, $X^2$ OH, or $X^1$ and $X^2$ together are O, OS(O)O or OS(O$_2$)O. The compound of formula (III) can be a single enantiomer or a mixture of enantiomers and/or diastereomers.

In a further aspect, the present invention provides a compound having the formula (III):

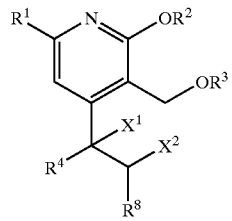

III wherein $R^1$ is hydrogen, fluorine, chlorine or SiR$^5$R$^6$R$^7$, wherein $R^5$, $R^6$, and $R^7$ are independently the same or different an alkyl group or an aryl group, $R^2$ is an alkyl group, $R^3$ is a protecting group, $R^4$ is an alkyl group, an allyl group, a propargyl group or a benzyl group, $R^8$ is —CHO, —CH$_2$OH, —CH$_2$OR$^9$, wherein $R^9$ is a protecting group, and $X^1$ is OH, $X^2$ is H or OH, or $X^1$ and $X^2$ together are O, OS(O)O or OS(O$_2$)O.

In a further aspect, the present invention provides a compound having the formula (VI):

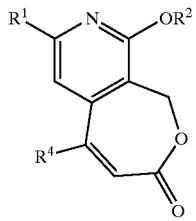

VI wherein $R^1$ is, for example, hydrogen, fluorine, chlorine or SiR$^5$R$^6$R$^7$ wherein $R^5$, $R^6$, and $R^7$ are independently the same or different an alkyl group (preferably a lower alkyl group) or an aryl group. $R^2$ is an alkyl group (preferably, a lower alkyl group). $R^3$ is a protecting group (for example, acetate, methoxymethyl or tert-butyldimethylsilyl). $R^4$ is an alkyl group (preferably, a lower alkyl group), an allyl group, a propargyl group or a benzyl group. Preferred embodiments of the compound of formula (VI) for use in the synthetic methods of the present invention include those in which $R^1$ is H or a trimethylsilyl group, $R^2$ is a lower alkyl group, and $R^4$ is an ethyl group.

In still another aspect, the present invention provides a compound having the formula (VII):

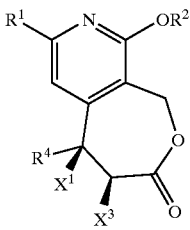

VII wherein $R^1$ is, for example, hydrogen, fluorine, chlorine or SiR$^5$R$^6$R$^7$ wherein $R^5$, $R^6$, and $R^7$ are independently the same or different an alkyl group (preferably a lower alkyl group) or an aryl group. $R^2$ is an alkyl group (preferably, a lower alkyl group). $R^3$ is a protecting group (for example, acetate, methoxymethyl or tert-butyldimethylsilyl). $R^4$ is an alkyl group (preferably, a lower alkyl group), an allyl group, a propargyl group or a benzyl group. In the compounds of formula (VII), $X^1$ is OH, $X^3$ is OH, or together $X^1$ and $X^3$ are O, OS(O)O or OS(O$_2$)O. The compound of formula (VII) can be a single enantiomer or a mixture of enantiomers and/or diastereomers. Preferred embodiments of the compound of formula (VII) for use in the synthetic methods of the present invention include those in which $R^1$ is H or a trimethylsilyl group, $R^2$ is a lower alkyl group, and $R^4$ is an ethyl group.

Reaction procedures such as the Wittig reaction, the Stille reaction, the Sharpless asymmetric epoxidation reaction, the Sharpless asymmetric dihydroxylation reaction, and the Jacobsen-Katsuki epoxidation reaction used in the present invention are well known in the art. Stille reactions are described, for example, in Farina, V., et al., *Org. React. (N.Y.)*, 50, 1, (1997), the disclosure of which is incorporated herein by reference. Sharpless epoxidation reactions are described in A. Pfenniger, *Synthesis*, 89 (1986);. Katsuki, T. and Martin, V. S., Org. React. (N.Y.), 48, 1, (1996), the disclosures of which are incorporated herein by reference. Sharpless asymmetric dihydroxylation reactions are described, for example, in Kolb, H. C., et al., Chem. Rev., 94, 2483, (1994), the disclosure of which is incorporated herein by reference. Jacobsen-Katsuki epoxidation reactions are described, for example, in Jacobsen, E. N., *Comprehensive Organometallic Chemistry II: A Review of the Literature 1982–1994*; Abel, E. W., et al., Pergamon: Oxford, UK,; Vol. 12; pp 1097 (1995), Linker, T., *Angew. Chem., Int. Ed. Engl.*, 36, 2060 (1997), the disclosures of which are incorporated herein by reference.

In general, the Wittig reaction is the coupling of a phosphorous ylide or a related species (for example, a phosphate or phosphonate anion) with an aldehyde or ketone to make an alkene. The Peterson olefination is the coupling of an α-silyl anion with an aldehyde or ketone to provide an alkene. This reaction may occur in one step, but a two step procedure through the intermediacy of a β-hydroxysilane is also common. This intermediate yields an alkene on treatment with acid or base.

The Stille reaction is the coupling of an organostannane and an organic halide (chloride, bromide or iodide) in the presence of a transition metal (often palladium) and a ligand (often a phosphine). The stannane is typically an aryltrialkylstannane, an alkenyltrialkylstannane or an acyltrialkylstannane and the aryl, alkenyl or acyl group is preferentially coupled. The halide is often an aryl halide or an alkenyl halide.

The Sharpless epoxidation is the conversion of an alkene to an enantiomerically enriched epoxide by treatment with a titanium compound (for example titanium tetraisopropoxide) in the presence of tartrate derivatives (for example, diethyl tartrate) and an oxidant (for example, tert-butyl hydroperoxide). Other compounds and additives are sometimes used to accelerate the reaction or increase the ee.

The Sharpless asymmetric dihydroxylation (SAD or sometimes AD) is the conversion of an alkene to an enantiomerically enriched 1,2-diol by treatment with an osmium compound (for example, potassium osmate or osmium tetraoxide) in the presence of one of many ligands derived from the quinine family of alkaloids, and oxidant (for example, tert-butyl hydroperoxide or potassium ferricyamide) and (optionally) other additives (for example, methane sulfonamide) to accelerate the reaction and/or increase the ee. Complete commercial preparations of reagents for the Sharpless epoxidation are available under the "AD-MIX" name, but many other ligands, oxidants and additives are also readily available.

The Jacobsen-Katsuki (or sometimes Jacobsen) epoxidation is the conversion of an alkene to an enantiomerically enriched epoxide by treatment with a manganese complex bearing, for example, a chiral SALEN ligand, in the presence of an oxidant and (optionally) other additives to accelerate the reaction and increase the ee.

BRIEF DESCRIPTION OF THE DRAWINGS

FIG. 1 illustrates the general structural formulas of camptothecins, silatecans, homocamptothecins and homosilatecans.

FIG. 2 illustrates the enantioselective synthesis of homocamptothecins and homosilatecans from the intermediates of FIG. 3.

FIG. 3 illustrates one embodiment of the enantioselective synthesis of an intermediate in the synthesis of homocamptothecins and homosilatecans.

FIG. 4 illustrates a variant of one embodiment of the enantioselective synthesis of FIG. 3.

FIG. 5 illustrates a representative example of a process of the present invention to increase the enantiopurity of beta-hydroxy lactones.

DETAILED DESCRIPTION OF THE INVENTION

As described above, a number of processes for the racemic synthesis of homocamptothecins and homosilatecans have been developed. The present invention provides intermediates and methods of synthesis for the first enantioselective synthetic route to homocamptothecins, including homosilatecans.

The terms "alkyl", "aryl" and other groups set forth herein refer generally to both unsubstituted and substituted groups unless specified to the contrary. Unless otherwise specified, alkyl groups are hydrocarbon groups and are preferably $C_1$–$C_{15}$ (that is, having 1 to 15 carbon atoms) alkyl groups, and more preferably $C_1$–$C_{10}$ alkyl groups, and can be branched or unbranched, acyclic or cyclic. "Lower alkyl" groups are $C_1$–$C_6$ alkyl groups. The above definition of an alkyl group and other definitions apply also when the group is a substituent on another group (for example, an alkyl group as a substituent of an alkylamino group or a dialkylamino group). The term "aryl" refers to phenyl or naphthyl.

Certain groups such as hydroxy groups, amino groups and/or other groups of certain compounds of the present invention and certain compounds used in the methods of the present invention can be protected using protective groups as known in the art. Such protective groups include, but are not limited to, —SiR$^5$R$^6$R$^7$ wherein R$^5$, R$^6$, and R$^7$ are independently the same or different an alkyl group (preferably a lower alkyl group) or an aryl group; CHR$^x$OR$^y$ where R$^x$ is H or alkyl (preferably lower alkyl, and more preferably methyl) and R$^y$ is alkyl (preferably lower alkyl) or CH$_2$C$_6$H$_3$R$^a$R$^b$ wherein R$^a$ and R$^b$ are independently the same or different, ortho, meta or para H, alkyl (preferably lower alkyl), alkoxy, nitro, cyano, halo, phenyl, trifluoromethyl or azido; CH$_2$CH$_2$OR$^{11}$ where R$^{11}$ is alkyl, CH$_2$CH$_2$SiR$^5$R$^6$R$^7$ or CH$_2$CCl$_3$; 2-tetrahydropyranyl; 4methoxy-2-tetrahydropyranyl; 2-tetrahydrofuranyl; CH$_2$SR$^c$ where R$^c$ is alkyl (preferably lower alkyl); CH$_2$CH$_2$SiR$^5$R$^6$R$^7$; a tert-butyl group; CH$_2$C$_6$H$_3$R$^d$R$^e$ wherein R$^d$ and R$^e$ are independently the same or different, ortho, meta, or para H, alkyl (preferably lower alkyl), alkoxy, nitro, cyano, halo, phenyl, trifluoromethyl or azido; or —C(O)R$^{12}$ wherein R$^{12}$ is H, alkyl (preferably lower alkyl), haloalkyl, aryl, alkoxy or $OCH_2C_6H_3R^fR^g$, wherein $R^f$ and $R^g$ are independently the same or different, ortho, meta, or para H, alkyl (preferably lower alkyl), alkoxy, nitro, cyano, halo, phenyl, trifluoromethyl or azido. Other suitable protecting groups as known to those skilled in the art are disclosed, for example, in Greene, T., Wuts, P. G. M., *Protective Groups in Organic Synthesis*, Wiley (1991), the disclosure of which is incorporated herein by reference.

Preferred protecting groups for hydroxy groups of compounds of the present invention and compounds used in the methods of the present invention include, but are not limited to, $SiR^5R^6R^7$ wherein $R^5$, $R^6$, and $R^7$ are independently the same or different an alkyl group (preferably a lower alkyl group) or an aryl group; a benzyl group or a substituted benzyl group; a formyl group; an acyl group (—$OCR^{13}$, wherein $R^{13}$ is for example, an alkyl group or an aryl group—for example, acetyl or benzoyl); an alkoxycarbonyl group (—$C(O)OR^{14}$, wherein $R^{14}$ is an alkyl group—for example, —C(O)OMe); an alkoxyalkyl group (for example, methoxymethyl 2-methoxyethoxymethyl, 1-ethoxyethyl or tetrahydropyranyl); or a thioalkyl group.

An important intermediate in the synthesis of the present invention is iodopyridone 12, which is in turn prepared from trimethylsilyl pyridine 10a by the steps of iododesilylation and demethylation (FIG. 2a). One embodiment of a novel enantioselective route to 12 is summarized in FIG. 3. In this embodiment, the route to the (20R)-homocamptothecin family includes generally the application of the Stille reaction and Sharpless asymmetric epoxidation as described above. The reactions have, for example, been performed on a relatively large scale (20 g) for the preparation of enantiomerically enriched homosilatecan libraries.

The synthesis of the DE-ring fragment (iodopyridone 12) of the homocamptothecin structure begins with aldehyde 1a, a known intermediate in the total synthesis of CPT via cascade radical annulation. Treatment with $NaBH_4$ followed by protection of the resulting alcohol as its methoxymethyl (MOM) ether furnished 3a in 70% yield (two steps). Subsequent Stille coupling reaction under Corey's conditions followed by reduction with LAH gave allylic alcohol 5a in 72% yield over two steps. Corey's conditions are set forth, for example, in, for example, Han, et al., *J. Am. Chem. Soc.*, 121, 7, 600 (1999). Sharpless asymmetric epoxidation of 5a using (+)-diethyl tartrate led to 6a in 90% ee (enantiomeric excess, determined using a Chiralcel OD-H column). Epoxide 6a was then converted to TMS-lactone 10a via a four step sequence including: (i) regioselective opening of the epoxide with LAH; (ii) Dess Martin oxidation; (iii) further oxidation with $NaClO_2$; (iv) MOM ether deprotection and in situ cyclization with TFA (44% overall yield from 3a). With enantioenriched 10a in hand, the remainder of the steps parallel generally the prior racemic synthesis. See U.S. Pat. Nos. 6,136,978, 6,150,343, 6,207,832 and 6,211,371. Lactone 10a was subjected to ICl mediated iododesilylation followed by demethylation with iodotrimethylsilane (TMSI) generated in situ to provide iodopyridone 12.

Likewise, intermediate 10b (FIG. 2b) can be made starting from 1b. Compound 10b is converted to 11 by demethylation with TMSI.

FIG. 3 illustrates only one of many different ways in which the compounds and processes of the current invention can be combined to make key intermediates like 10a,b. An illustrative variant is shown in FIG. 4. Iodide 3a was converted to the magnesium reagent by treatment with iPrMgCl. Transmetallation with CuCN/LiCl followed by addition of propionoyl chloride provided ketone 18. Wittig reaction of 18 provided mixtures of 19E and 19Z in ratios that varied somewhat with reaction conditions. These isomers were separated by column chromatography to give the pure E and Z isomers. Reduction of 19E with LAH gave 5aE (shown in FIG. 3) in 96% yield while similar reduction of of 19Z give 5aZ (not shown). The Sharpless epoxidation of 5aZ under the conditions shown in FIG. 3 gave only about 30% ee, so the use of the E isomer as shown in FIG. 3 is preferred.

FIG. 5 shows an illustrative example of the method for increasing the enantiopurity of beta-hydroxy lactones (including homocamptothecins). Racemic lactone (rac)-10a was dehydrated with Burgess reagent (methoxycarbonylsulfamoyltriethylammonium hydroxide) at room temperature in THF to provide unsaturated lactone 20 in 83% yield. Sharpless asymmetric dihydroxylation under standard conditions (see Examples) then provided diol (+)-21 in 48% yield and 67% ee. The secondary hydroxy group can then be activated and removed (as described in Curran, D. P.; Ko, S. B., *J. Org. Chem.*, 59, 6139–6141 (1994), the disclosure of which is incorporated herein by reference) by, for example, conversion to the tosylate or mesylate, bromide displacement and reduction with the hydride. Alternatively, the tosylate or a related activated intermediate can be reduced by, for example, samarium diiodide.

EXAMPLES

Example 1

[4-Iodo-2-methoxy-6-(trimethylsilanyl)pyridin-3-yl] methanol (2a)

To a solution of $NaBH_4$ (1.1 g, 26.4 mmol) in EtOH (100 mL) at –40° C. was slowly added a solution of 4-iodo-2-methoxy-6-trimethylsilanyl-3-pyridinecarboxaldehyde 1 (31.8 g, 94.9 mmol) in EtOH (50 mL). See Josien, H.; Ko, S.-B.; Bom, D.; Curran, D. P. *Chem. Eur. J.*, 67 (1998). After stirring for 1 h, the reaction mixture was carefully quenched with brine and then extracted 3 times with $Et_2O$. The combined organic extracts were dried over $MgSO_4$. The solvent was removed under reduced pressure and the residue purified by flash chromatography (gradient hexane to hexane-EtOAc 91:9) to afford 2a (25.1 g, 78% yield) as a clear oil. $^1H$ NMR (300 MHz, $CDCl_3$) δ0.28 (s, 9H), 2.5 (bs, 1H), 4.01 (s, 3H), 4.8 (s, 2H), 7.5 (s, 1H); $^{13}C$ NMR (75 MHz, $CDCl_3$) δ–1.99, 53.78, 65.32, 11.65, 125.34, 133.19, 160.9, 165.81; IR (film, NaCl, $cm^{-1}$) 3485, 2960, 1580, 1450, 1039, 839; LRMS (70 eV, EI) m/z (rel int %) 337 ($M^+$), 322 (100), 306, 194, 180, 73. HRMS m/z calcd for $C_{10}H_{16}NO_2SiI$ ($M^+$) 336.9996, found 337.000.

Example 2

4-Iodo-2-methoxy-3-methoxymethoxymethyl-6-(trimethylsilanyl)pyridine (3a)

MOMCl (2.0 mL, 26.7 mmol) was added dropwise to a 0° C. solution of 2a (3 g, 8.9 mmol) and $^iPr_2EtN$ (4.6 mL, 26.7 mmol) in dry $CH_2Cl_2$ (35 mL). The resulting mixture was allowed to warm to room temperature and stirred overnight. The reaction was quenched with 5% aq. $NaHCO_3$ solution and the product was extracted with $CH_2Cl_2$. The combined organic phases were washed with brine, dried over $MgSO_4$ and concentrated under reduced pressure to give 3.0 g (88% yield) of the crude product 3a as an orange oil. The crude product was sufficiently pure for the subsequent reaction. $^1H$ NMR (300 MHz, $CDCl_3$) δ0.27 (s, 9H), 3.46 (s, 3H), 3.98

(s, 3H), 4.71 (s, 2H), 4.75 (s, 2H), 7.51 (s, 1H); $^{13}$C NMR (75 MHz, CDCl$_3$) δ–2.08, 53.79, 55.53, 67.85, 96.39, 113.84, 122.6, 132.98, 161.43, 166.37; IR (film, NaCl, cm$^{-1}$) 2946, 1528, 1340, 1042, 840; LRMS (70 eV, EI) m/z (rel int %) 381 (M$^+$), 366, 336, 320, 306, 169, 128, 84 (100), 73. HRMS m/z calcd for C$_{12}$H$_{20}$NO$_3$SiI (M$^+$) 381.0257, found 381.0241.

Example 3

3-[2-Methoxy-3-methoxymethoxymethyl-6-(trimethylsilanyl)pyridin-4-yl]pent-2-enoic acid ethyl ester (4a)

A round bottom flask was charged with LiCl (66.6 mg, 1.57 mmol) and flamed dried under vacuum. Pd(PPh$_3$)$_4$ (32.6 mg, 0.026 mmol), CuCl (129.6 mg, 1.31 mmol) and DMSO (2.0 mL) were added and the mixture was degassed. 3a (100 mg, 0.262 mmol) was added, followed by ethyl (E)-3-(tri-n-butylstannyl)-2-pentenoate (131.4 mg, 0.314 mmol) and the resulting mixture was degassed. See Piers, E., et al., *Can. J. Chem.*, 2058 (1992). The reaction mixture was then heated at 60° C. for 17 h. After cooling, the reaction was diluted with Et$_2$O (30 mL) and washed with a mixture of brine (40 mL) and 5% aq. NH$_4$OH (8 mL). The aqueous layer was extracted 3 times with Et$_2$O. The combined organic extracts were dried over MgSO$_4$ and concentrated under reduced pressure. The crude product was purified by flash chromatography (gradient hexane to hexane-EtOAc 95:5) to yield 4a (80 mg, 80%) as a clear oil. $^1$H NMR (300 MHz, CDCl$_3$) δ0.28 (s, 3H), 0.99 (t, J=7.5 Hz, 3H), 1.3 (t, J=7.1 Hz, 3H), 2.98 (q, J=7.5 Hz, 2H), 3.42 (s, 3H), 4.02 (s, 3H), 4.2 (q, J=7.1 Hz, 2H), 4.47 (s, 2H), 4.72 (s, 2H), 5.79 (s, 1H), 6.84 (s, 1H); $^{13}$C NMR (75 MHz, CDCl$_3$) δ–1.96, 12.3, 14.25, 26.57, 53.58, 55.35, 60.01, 61.95, 9672, 115.49, 119.49, 121.17, 151.15, 159.9, 162.21, 164.81, 165.83; IR (film, NaCl, cm$^{-1}$) 2; LRMS (70 eV, EI) m/z (rel int %) 381 (M$^+$), 366, 336, 320, 308 (100), 290, 262, 246, 89, 73. HRMS m/z calcd for C$_{19}$H$_{31}$NO$_5$Si (M$^+$) 381.1976, found 381.19667.

Example 4

3-[2-Methoxy-3-methoxymethoxymethyl-6-(trimethylsilanyl)pyridin-4-yl]pent-2-en-1-ol (5a)

To a –78° C. mixture of 4a (100 mg, 0.26 mmol) in Et$_2$O (3 mL) was slowly added LAH (0.26 mL, 0.26 mmol, 1.0 M solution in Et$_2$O). The resulting mixture was allowed to warm to 0° C. and then quenched by addition of a chilled saturated aq. solution of potassium sodium tartrate. The aqueous layer was extracted 3 times with Et$_2$O. The combined organic extracts were dried over MgSO$_4$ and concentrated under reduced pressure. The crude product was purified by flash chromatography (hexane-EtOAc 75:25) to yield 5a (80 mg, 90%) as a colorless oil. $^1$H NMR (300 MHz, CDCl$_3$) δ0.27 (s, 9H), 0.91 (t, J=7.5 Hz, 3H), 2.43 (q, J=7.5 Hz, 2H), 3.43 (s, 3H), 4.01 (s, 3H), 4.33 (d, J=6.9 Hz, 2H), 4.53 (s, 2H), 4.69 (s, 2H), 5.61 (t, J=6.9 Hz, 1H), 6.87 (s, 1H); $^{13}$C NMR (75 MHz, CDCl$_3$) δ–1.97, 13.01, 25.27, 53.37, 55.32, 58.79, 61.58, 95.91, 115.9, 122.3, 128.7, 142.36, 152.2, 162.3, 164.3; IR (film, NaCl, cm$^{-1}$) 3388, 2949, 1576, 1450, 1340, 1042, 854; LRMS (70 eV, EI) m/z (rel int %) 339 (M$^+$), 324, 308, 294, 277, 262 (100), 248, 232, 218, 188, 174, 117, 89, 73, 59. HRMS m/z calcd for C$_{17}$H$_{29}$NO$_2$Si (M$^+$) 339.1866, found 339.1861.

Example 5

(+)-(2R, 3R)-{3-Ethyl-3-[2-methoxy-6-(trimethylsilanyl)pyridin-4-yl]-oxiranyl}-methanol (6a)

To a solution of 5a (937 mg, 2.76 mmol) and activated 4 Å molecular sieves (280 mg) in CH$_2$Cl$_2$ (26 mL) at –20° C. was added diethyl-L(+)-tartrate (568 mg, 2.75 mmol), and Ti(O$^i$Pr)$_4$ (629 mg, 2.2 mmol). After stirring for 1 h, $^t$BuOOH (1.1 mL, 5.0–6.0 M in decane, predried over 4 Å molecular sieves for 1 h) was added with a syringe. The reaction mixture was kept in the freezer at –20° C. for 60 h. The solution was removed from the freezer, diluted with Et$_2$O (5.2 mL) and quenched with a saturated Na$_2$SO$_4$ solution (2.6 mL). The resulting heterogeneous mixture was stirred and allowed to warm to room temperature for 2 h. Then it was filtered through a celite pad (washing with hot EtOAc several times). The combined filtrates were concentrated under vacuum. The residue was dissolved in Et$_2$O (13 mL) at 0° C. and a 1N NaOH solution saturated with NaCl was added (8 mL). The two-phase mixture was vigorously stirred at 0° C. for 1 h and then transfered to a separatory funnel. The aqueous layer was separated and extracted 3 times with EtOAc. The combined organic extracts were dried over MgSO$_4$ and concentrated under reduced pressure to give 651 mg (66% yield) of the crude product 6a as a clear oil with 92% ee and sufficiently pure for the subsequent reaction. Epoxide 6a was analyzed for enantiomeric purity using a Chiralcel OD-H column with 98.5:1.5 hexane:$^i$PrOH as the eluent, using the racemate as the standard. $^1$H NMR (300 MHz, CDCl$_3$) δ0.27 (s, 9H), 0.9 (t, J=7.5 Hz, 3H), 1.79 (m, 1H), 1.97 (m, 1H), 3.23 (t, J=5.8 Hz, 1H), 3.45 (s, 3H), 3.9 (m, 2H), 3.99 (s, 3H), 4.64–4.72 (m, 4H), 7.09 (s, 1H); $^{13}$C NMR (75 MHz, CDCl$_3$) δ–1.93, 9.18, 25.63, 29.66, 53.42, 55.59, 60.64, 61.21, 63.46, 64.63, 96.44, 115.45, 121.32, 148.36, 161.89, 165.16; IR (film, NaCl, cm$^{-1}$) 3463, 2945, 1562, 1451, 1345, 1041, 840; LRMS (70 eV, EI) m/z (rel int %) 355 (M$^+$), 340, 324, 310, 294, 280, 262, 250, 89, 73, 57. HRMS m/z calcd for C$_{17}$H$_{29}$NO$_5$Si (M$^+$) 355.1815, found 355.1812, [α]$^{23}_D$=+28(c=0.25, CH$_2$Cl$_2$).

Example 6

(–)-(3R)-3-[2-Methoxy-3-methoxymethoxymethyl-6-(trimethylsilanyl)pyridin-4-yl]-pent-2-en-1-ol (7a)

LAH (0.3 mL, 0.3 mmol) was slowly added to a 0° C. mixture of 6a (144 mg, 0.4 mmol) in Et$_2$O (9 mL). The resulting mixture was allowed to warm to room temperature and stirred overnight. The reaction was quenched with a saturated aq. solution of potassium sodium tartrate. The aqueous layer was extracted 3 times with Et$_2$O. The combined organic phases were washed with brine, dried over MgSO$_4$ and concentrated under reduced pressure to give 144 mg (99% yield) of the crude product 7a as colorless oil. The crude product was sufficiently pure for the subsequent reaction. $^1$H NMR (300 MHz, CDCl$_3$) δ0.28 (s, 9H), 0.78 (t, J=7.4 Hz, 3H), 1.9 (m, 2H), 2.13 (m, 2H), 3.43 (s, 3H), 3.59 (m, 1H), 3.7 (m, 1H), 4.0 (s, 3H), 4.71 (s, 2H), 4.89 (d, J=10.6 Hz, 1H), 5.09 (d, J=10.6 Hz, 1H), 6.91 (s, 1H); $^{13}$C NMR (75 MHz, CDCl$_3$) δ–1.94, 7.64, 36.44, 43.73, 48.78, 53.61, 55.73, 60.06, 69.97, 80.87, 96.23, 116.71, 121.23, 153.73, 162.64, 164.08; IR (film, NaCl, cm$^{-1}$) 3383, 2962, 1545, 1342, 1038, 839; LRMS (70 eV, EI) m/z (rel int %) 339 (M$^+$–H$_2$O), 324, 308, 294, 266, 250, 85, 73(100), 57. HRMS m/z calcd for C$_{17}$H$_{29}$NO$_4$Si (M$^+$–H$_2$O) 339.1866, found 339.1876; [α]$^{23}_D$=–1.9(c=1.05, CH$_2$Cl$_2$).

Example 7

(–)-(3R)-3-Hydroxy-3-[2-methoxy-3-methoxymethoxymethyl-6-(trimethylsilanyl)pyridin-4-yl]pentanoic acid (9a)

To a mixture of 7a (0.75 g, 2.1 mmol) in CH$_2$Cl$_2$ (30 mL) was added Dess-Martin periodinane (1.4 g, 3.3 mmol). The mixture was stirred at rt for 3 h and then poured into a well-stirred mixture of sat. $Na_2S_2O_3$ (15 mL) and sat. $NaHCO_3$ (15 mL). The layers were separated after 30 min. The aqueous layer was extracted 3 times with $Et_2O$. The combined organic extracts were washed with sat. $NaHCO_3$, brine, dried over $MgSO_4$ and concentrated under vacuum to give the crude aldehyde 8a (750 mg, 2.11 mmol), which was used immediately after workup.

To a solution of the aldehyde 8a (750 mg, 2.11 mmol) in tert-butyl alcohol (40 mL) was added 2-methyl-2-butene (12 mL). To this mixture was added dropwise a solution containing sodium chlorite (1.7 g, 18.8 mmol) and sodium dihydrogen phosphate (2 g, 14.5 mmol) in $H_2O$ (20 mL). The resulting mixture was stirred at rt for 16 h, concentrated under vacuum, diluted with water and extracted with EtOAc. The aqueous layer was acidified (pH 3.5) with 5% HCl and extracted with EtOAc. The combined organic layers were washed with brine, dried over $Na_2SO_4$ and concentrated under vacuum to give the crude acid 9a (740 mg, 94%) as a clear oil and sufficiently pure for the subsequent reaction. $^1H$ NMR (300 MHz, $CDCl_3$) δ0.27 (s, 9H), 0.84 (t, J=7.3 Hz, 3H), 1.91 (q, J=7.3 Hz, 2H), 2.89 (d, J=15.8 Hz, 1H), 3.1 (d, J=15.8 Hz, 1H), 3.43 (s, 3H), 3.97 (s, 3H), 4.73 (s, 2H), 4.9 (d, J=10.6 Hz, 1H), 5.0 (d, J=10.6 Hz, 1H), 6.95 (s, 1H); $^{13}C$ NMR (75 MHz, $CDCl_3$) δ−2.00, 8.0, 35.61, 45.73, 53.58, 55.63, 61.06, 77.25, 96.26, 116.06, 120.37, 152.46, 162.88, 164.72, 175.15; IR (film, NaCl, $cm^{-1}$) 3474, 1712, 1345, 1036, 840; LRMS (70 eV, EI) m/z (rel int %) 353 ($M^+-H_2O$), 326, 308 (100), 294, 280, 262, 250, 236, 190, 89, 73, 57. HRMS m/z calcd for $C_{17}H_{27}O_5Si$ ($M^+-H_2O$) 353.1659, found 353.1655; $[α]^{23}_D$=−6.8(c=0.54, $CH_2Cl_2$).

Example 8

(+)-(5R)-5-Ethyl-5-hydroxy-1-methoxy-3-(trimethylsilanyl)-5,9-dihydro-6H-8-oxa-2-aza-benzocyclohepten-7-one (10a)

To a round bottom flask was added 9a (0.74 g, 1.99 mmol) followed by TFA (50 mL). The mixture was stirred at rt for 16 h and then concentrated under reduced pressure. The residue was dissolved in $Et_2O$ and neutralized with sat. $NaHCO_3$. The organic phase was dried over $MgSO_4$ and concentrated under reduced pressure. The crude product was purified by flash chromatography (hexane-EtOAc 75:25) to yield 10a (0.43 g, 70%) with 90% ee as a white foam; $[α]^{23}_D$=+45.1 (c=0.86, $CH_2Cl_2$). Lactone 10a was analyzed for enantiomeric purity using a Chiralcel OD-H column with 92:8 hexane:$^iPrOH$ as the eluent, using the racemate as the standard.

Example 9

4-Iodo-2-methoxy-pyridine-3-carbaldehyde (1b)

Methyllithium in diethyl ether (1.4 M, 23.5 mL, 33 mmol) was added to a solution of 2-methoxypyridine (1.93 mL, 18.3 mmol) in THF (120 mL) at −40° C. To this mixture was added diisopropylamine (0.128 mL, 0.9 mmol) upon which the mixture turned yellowish orange. After warming to 0° C. and stirring for 3 h, the mixture was cooled to −78° C. and N,N,N'-trimethyl-N'-formylethylenediamine (2.62 g, 20 mmol) was added slowly. The mixture was allowed to warm to −40° C. nBuLi in hexanes (1.6M, 22.9 mL, 36.6 mmol) was injected and the mixture was stirred for 3 h at −30° C. A solution of $I_2$ (11.2 g, 44 mmol) in THF (70 mL) was then added dropwise through a dropping funnel at −78° C. with vigorous stirring. After 30 min, the resulting mixture was allowed to warm slowly to 0° C. (1 h), poured into 5% $Na_2SO_3$ (250 mL) and extracted with $Et_2O$ (3×150 mL) and the residue obtained after removal of the solvents was subjected to flash chromatography (hexanes/ethyl acetate 95:5) to provide 1b as a yellow oil (1.9 g, 40%). IR ($CH_2Cl_2$, NaCl, $cm^{-1}$): 1703, 1551, 1462, 1368, 1298, 1265, 1017, 847, 736; $^1H$ NMR (300 MHz, $CDCl_3$) δ4.06 (s, 3H), 7.54 (d, J=5.3 Hz, 1H), 7.86 (d, J=5.3 Hz, 1H), 10.21 (s, 1H); $^{13}C$ NMR (75 MHz, $CDCl_3$) δ54.61, 108.75, 119.4, 130.52, 150.97, 164.44, 190.38; HRMS (EI): m/z calcd for $C_7H_6INO_2$ ($M^+$) 262.9443, found 262.9431; LRMS (EI) m/z 263 ($M^+$, 100), 234 (80), 205 (30), 127 (30), 93 (28), 78 (72).

Example 10

(4-Iodo-2-methoxy-pyridin-3-yl)methanol (2b)

Following the procedure in Example 1, the reaction was carried out with 1b (1.88 g, 7.1 mmol) and $NaBH_4$ (0.135 g, 3.56 mmol) in EtOH (40 mL) to afford 2b as a pale yellow oil (1.83 g, 97%). The crude product was sufficiently pure for the subsequent reaction. IR ($CH_2Cl_2$, NaCl, $cm^{-1}$) 3391, 2946, 1561, 1459, 1380, 1019, 805; $^1H$ NMR (300 MHz, $CDCl_3$) δ2.43 (t, J=7 Hz, 1H), 3.99 (s, 3H), 4.82 (d, J=7 Hz, 2H), 7.35 (d, J=5.4 Hz, 1H), 7.7 (d, J=5.4 Hz, 1H); $^{13}C$ NMR (75 MHz, $CDCl_3$) δ54.29, 64.90, 112.12, 126.50, 128.15, 146.59, 161.71; HRMS (EI) m/z calcd for $C_7H_8NO_2I$ ($M^+$) 264.9600, found 264.9598; LRMS (EI) m/z 265 ($M^+$, 53), 250(84), 138(30), 84(100), 78(30).

Example 11

4-Iodo-2-methoxy-3-methoxymethoxymethylpyridine (3b)

Following the procedure in Example 2, the reaction was carried out with 2b (1.77 g, 6.68 mmol), MOMCl (1.52 mL, 20 mmol) and $^iPr_2EtN$ (3.49 mL, 20 mmol) in dry $CH_2Cl_2$ (40 mL) to afford 3b as an orange-yellow oil (2.06 g, 100%). The crude product was sufficiently pure for the subsequent reaction. IR ($CH_2Cl_2$, NaCl, $cm^{-1}$) 2949, 1561, 1459, 1380, 1265, 1039, 741; $^1H$ NMR (300 MHz, $CDCl_3$) δ3.45 (s, 3H), 3.96 (s, 3H), 4.72 (s, 2H), 4.75 (s, 2H), 7.35 (d,J=5.4 Hz, 1H), 7.71 (d,J=5.4 Hz, 1H); $^{13}C$ NMR (75 MHz, $CDCl_3$) δ54.35, 55.80, 67.89, 96.70, 114.20, 123.97, 128.10, 147.11, 162.39; HRMS (EI) m/z calcd for $C_9H_{12}NO_3I$ ($M^+$) 308.9862, found 308.9860; LRMS (EI) m/z 309($M^+$, 19), 277(20), 264(45), 248(100), 218(68), 152(39), 92(50), 79(35).

Example 12

3-(2-Methoxy-3-methoxymethoxymethyl-pyridin-4-yl)pent-2-enoic acid ethyl ester (4b)

Following the procedure in Example 3, the reaction was carried out with 3b (1.0 g, 3.23 mmol), LiCl, predried under vacuum at 120° C. for a period of 24 h (0.82 g, 19.4 mmol), CuCl (1.60 g, 16.2 mmol), $Pd(PPh_3)_4$ (0.19 g, 0.16 mmol) and ethyl (E)-3-(tributylstannyl)-2-pentenoate (1.62 g, 3.88 mmol) in dry DMSO (35 mL). The crude product was subjected to flash chromatography (hexanes/ethyl acetate 95:5) to afford 4b as a yellow oil (0.82 g, 82%). IR ($CH_2Cl_2$, NaCl,$cm^{-1}$) 2982, 1713, 1640, 1593, 1560, 1453, 1392, 1266, 1186, 1040, 743; $^1H$ NMR (300 MHz, $CDCl_3$) δ0.99 (t, J=7.6 Hz, 3H), 1.30 (t, J=7.1 Hz, 3H), 2.99 (q, J=7.6 Hz, 2H), 3.43 (s, 3H), 4.01 (s, 3H), 4.21 (q, J=7 Hz, 2H), 4.49 (s, 2H), 4.73 (s, 2H), 5.81 (s, 1H), 6.69 (d, J=5 Hz, 1H), 8.11 (d, J=5 Hz, 1H); $^{13}C$ NMR (75 MHz, $CDCl_3$) δ12.46, 14.43, 26.58, 54.05, 55.58, 60.26, 62.05, 96.96, 116.27, 116.85, 120.00, 146.36, 153.34, 159.37, 163.42, 165.90; HRMS (EI) m/z calcd for $C_{16}H_{23}NO_5$ ($M^+$) 309.1576, found 309.1587; LRMS (EI) m/z 309($M^+$, 32), 277(42), 236(100), 190(84), 174(73), 160(22), 77(10).

Example 13

3-(2-Methoxy-3-methoxymethoxymethylpyridin-4-yl)pent-2-en-1-ol (5b)

Following the procedure in Example 4, the reaction was carried out with 4b (1.2 g, 3.88 mmol) and a 1 M solution of LAH in diethyl ether (9.7 mL, 9.7 mmol) to afford 5b as a very pale yellow oil (0.84 g, 81%). The crude product was sufficiently pure for the subsequent reaction. IR ($CH_2Cl_2$, NaCl,cm$^{-1}$) 3383, 2945, 1594, 1555, 1452, 1391, 1320, 1268, 1148, 1038, 739, 541; $^1$H NMR (300 MHz, $CDCl_3$) δ0.92 (t, J=7.6 Hz, 3H), 2.44 (q, J=7.6 Hz, 2H), 3.44 (s, 3H), 4.00 (s, 3H), 4.33 (t, J=5.6 Hz, 2H), 4.55 (s, 2H), 4.70 (s, 2H), 5.63 (t, J=6.8 Hz, 1H), 6.68 (d, J=5.2 Hz, 1H), 8.07 (d, J=5.2 Hz, 1H); $^{13}$C NMR (75 MHz, $CDCl_3$) δ13.19, 15.46, 25.37, 53.98, 55.60, 59.02, 61.79, 96.25, 117.29, 129.39, 142.05, 146.12, 154.63, 163.60; HRMS (EI) m/z calcd for $C_{13}H_{18}NO_3$ 236.1287, found 236.1292; LRMS (EI) m/z 268(M+H, 38), 249(31), 236(62), 190(48), 176(100), 160 (35), 91(16), 77(15).

Example 14

(+)-(3R)-[3-Ethyl-3-(2-Methoxy-3-methoxymethoxymethyl-pyridin-4-yl)oxiranyl]methanol (6b)

Following the procedure in Example 5, the reaction was carried out with 5b (0.80 g, 3 mmol), Ti(O$^i$Pr)$_4$ (0.71 mL, 2.4 mmol), diethyl-L(+)-tartrate (0.51 mL, 3 mmol), $^t$BuOOH (0.95 mL, 5.0–6.0M in decane) and 4 Å molecular sieves (241 mg) in dry $CH_2Cl_2$ for 24 h to afford 6b as a yellow oil (754 mg, 89%) with 96% ee. The crude product was sufficiently pure for the subsequent reaction. Epoxide 6b was analyzed for enantiomeric purity using a Chiralcel OD-H column with 98:2 hexane/$^i$PrOH as the eluent with the racemate as the standard. IR ($CH_2Cl_2$, NaCl,cm$^{-1}$) 3408, 2980, 1765, 1607, 1457, 1410, 1393, 1266, 1040, 742, 546; $^1$H NMR (300 MHz, $CDCl_3$) δ0.92 (t, J=7.6 Hz, 3H), 1.82 (m, 1H), 1.99 (m, 1H), 3.24 (t, J=5.8 Hz, 1H), 3.46 (s, 3H), 3.90 (m, 2H), 3.99 (s, 3H), 4.71 (s, 2H), 4.73 (s, 2H), 6.93 (d,J=5.2 Hz, 1H), 8.12 (d, J=5.2 Hz, 1H); $^{13}$C NMR (75 MHz, $CDCl_3$) δ9.41, 25.73, 25.98, 54.06, 55.82, 60.80, 61.33, 63.72, 64.72, 96.70, 116.46, 116.83, 146.60, 150.98, 163.10; HRMS (EI) m/z calcd for $C_{14}H_{22}NO_5$ (M+H) 284.1498, found 284.1507; LRMS (EI) m/z 284(M+H, 58), 190(100), 178(73), 162(27), 148(27), 77(13); $[\alpha]_D^{23}$=+65.6 (c=0.25, $CH_2Cl_2$).

Example 15

(+)-(3R)-3-(2-Methoxy-3-methoxymethoxymethylpyridin-4-yl)-pentane-1,3-diol (7b)

Following the procedure in Example 6, the reaction was carried out with 6b (0.71 g, 2.5 mmol) and LAH in dry ether (50 nmL) for 24 h to afford 7b as colorless oil (0.54 g, 76%). The crude product was sufficiently pure for the subsequent reaction. IR ($CH_2Cl_2$, NaCl,cm$^{-1}$) 3391, 3056, 2984, 1593, 1446, 1382, 1265, 1037, 743, 546; $^1$H NMR (300 MHz, $CDCl_3$) δ0.79 (t, J=7.3 Hz, 3H), 1.91 (q,J=7.3 Hz, 2H), 2.15 (m, 2H), 3.42 (s, 3H), 3.60 (m, 1H), 3.74 (m, 1H), 3.98 (s, 3H), 4.71 (s, 2H), 4.89 (d, J=10.7 Hz, 1H), 5.10 (d, J=10.7 Hz, 1H), 6.77 (d,J=5.5 Hz, 1H), 8.05 (d, J=5.5 Hz, 1H); $^{13}$C NMR (75 MHz, $CDCl_3$) δ7.81, 36.65, 43.80, 54.14, 55.94, 60.20, 61.13, 80.93, 96.53, 116.33, 117.94, 146.17, 156.45, 163.82; HRMS (EI) m/z calcd for $C_{14}H_{24}NO_5$ ($M^++H$) 286.1654, found 286.1658; LRMS (EI) m/z 286 ($M^++H$, 39), 235(23), 222(86), 205(52), 194(74), 178(100), 150(49), 92(30), 77(15); $[\alpha]_D^{23}$=+0.185 (c=1.08, $CH_2Cl_2$).

Example 16

(+)-(3R)-3-Hydroxy-3-(2-methoxy-3-methoxymethoxymethylpyridin-4-yl)pentanal (8b)

To a mixture of 7b (0.5 g, 1.78 mmol) in $CH_2Cl_2$ (20 mL) was added Dess-Martin periodinane (1.2 g, 2.85 mmol). The mixture was stirred at rt for 3 h and then poured into a well-stirred mixture of satd. $Na_2S_2O_3$ (10 mL) and satd. $NaHCO_3$ (10 mL). The layers were separated after 30 min. The aqueous layer was extracted 3 times with diethyl ether. The combined organic extracts were washed with satd. $NaHCO_3$, brine, dried over $MgSO_4$ and concentrated under vacuum to give the crude aldehyde 8b (0.47 g, 89%) as pale yellow oil. The crude product was sufficiently pure for the subsequent reaction. IR ($CH_2Cl_2$, NaCl,cm$^{-1}$) 3380, 3057, 2982, 1763, 1655, 1596, 1422, 1264, 895, 735, 547; $^1$H NMR (300 MHz, $CDCl_3$) δ0.82 (t, J=7.4 Hz, 3H), 1.91 (m, 2H), 2.85 (d, J=15.9 Hz, 1H), 3.10 (d, J=15.9 Hz, 1H), 3.41 (s, 3H), 3.96 (s, 3H), 4.74 (s, 2H), 4.98 (q, J=10.9 Hz, 2H), 6.74 (d, J=5.5 Hz, 1H), 8.06 (d, J=5.5 Hz, 1H), 9.73 (s, 1H); $^{13}$C NMR (75 MHz, $CDCl_3$) δ7.94, 36.42, 54.23, 55.31, 55.99, 60.93, 77.90, 96.45, 115.82, 117.41, 146.55, 155.59, 163.85, 202.18; HRMS (EI) m/z calcd for $C_{14}H_{22}NO_5$ (M+H) 284.1498, found 284.1498; LRMS (ED) 284(M+H, 15), 265(25), 192(20), 178(72), 148(24), 84(100), 57(26); $[\alpha]_D^{23}$=−11.5 (c=0.125, $CH_2Cl_2$).

Example 17

(+)-(5R)-5-Ethyl-5-hydroxy-1-methoxy-5,6-dihydro-9H-8-oxa-2-aza-benzocyclohepten-7-one (10b)

To a solution of the aldehyde 8b (0.13 g, 0.46 mmol) in tert-butyl alcohol (7.1 mL) was added 2-methyl-2-butene (2.13 mL). To this mixture was added dropwise a solution of sodium chlorite (0.37 g, 4.13 mmol) and sodium dihydrogen phosphate (0.44 g, 3.2 mmol) in $H_2O$ (3.8 mL). The resulting mixture was stirred at rt for 36 h. The crude mixture was extracted with ethyl acetate. The aqueous layer was then acidified (pH~3.5) with dropwise addition of 5% HCl and subsequently extracted with ethyl acetate (in cases where a yellow coloration was observed, the mixture was washed with 5% sodium sulfite solution). The combined organic extracts were washed with brine, dried over sodium sulfate and concentrated under vacuum to give the crude product 9b (0.12 g, 84%) as a light green oil which was used immediately after the workup.

To a round-bottom flask was added 9b (0.11 g, 0.38 mmol) followed by TFA (8 mL). The mixture was stirred for 24 h at rt. The mixture was then neutralized with satd. $NaHCO_3$ (pH~8) and extracted with diethyl ether (3×6 mL). The combined organic extracts were dried over $MgSO_4$ and concentrated under reduced pressure to afford 10b as yellowish brown oil (72 mg, 80%) which was sufficiently pure for the subsequent reaction. IR (MeOH, NaCl,cm$^{-1}$) 3390, 2958, 1725, 1683, 1596, 1377, 1204, 1140, 1041; $^1$H NMR (300 MHz, $CD_3OD$) δ0.84 (t, J=7.4 Hz, 3H), 1.85 (q, J=7.4

Hz, 2H), 3.01 (d, J=13.9 Hz, 1H), 3.41 (d, J=13.9 Hz, 1H), 3.94 (s, 3H), 5.29 (d, J=15.2 Hz, 1H), 5.44 (d, J=15.2 Hz, 1H), 7.15 (d,J=5.5 Hz, 1H), 8.13 (d, J=5.5 Hz, 1H); $^{13}$C NMR (75 MHz, CD$_3$OD) δ9.01, 38.48, 43.81, 54.97, 61.36, 62.66, 74.68, 117.12, 147.84, 155.98, 161.91, 173.06; HRMS (EI) m/z calcd for C$_{12}$H$_{15}$NO$_4$ (M$^+$) 237.1001, found 237.0996; LRMS (EI) m/z 237 (M$^+$, 75), 208(22), 166(100), 136(25), 106(7), 77(7); $[α]_D^{23}$=+3.0 (c=0.1, MeOH).

Example 18

(+)-(5R)-5-Ethyl-5-hydroxy-2,5,6,9-tetrahydro-8-oxa-2-aza-benzocycloheptene-1,7-dione (11)

To a dry round-bottom flask was added lactone 10b (0.07 g, 0.3 mmol) followed by dry acetonitrile (1 mL). Sodium iodide (0.07 g, 0.49 mmol) was added followed by chlorotrimethylsilane (0.06 mL, 0.49 mmol). The resulting mixture was stirred at rt for 15 min at which point H$_2$O was added (2.7 μL, 0.15 mmol) and the reaction mixture was heated to 60° C. for 7 h. The mixture was then poured into a 1:1 solution of 5% sodium sulfite/brine (7 mL) and then quickly extracted with ethyl acetate (4×5 mL). The organic layer was dried over MgSO$_4$ and concentrated under reduced pressure. The crude product was subjected to flash chromatography (MeOH/CH$_2$Cl$_2$ 5:95) to afford pure 11 as pale yellow oil (10.4 mg, 16%). IR (MeOH, NaCl,cm$^{-1}$) 3370(br), 1655, 1049, 1025, 823, 768; $^1$H NMR (300 MHz, CD$_3$OD) δ0.91 (t, J=7.5 Hz, 3H), 1.82 (m, 2H), 3.10 (d, J=13.8 Hz, 1H), 3.40 (d, J=13.8 Hz, 1H), 5.30 (d, J=15.2 Hz, 1H), 5.46 (d, J=15.2 Hz, 1H), 6.57 (d, J=7 Hz, 1H), 7.35 (d, J=7 Hz, 1H); $^{13}$C NMR (75 MHz, CDCl$_3$/CD$_3$OD) δ6.76, 35.22, 41.46, 60.98, 72.43, 105.93, 122.42, 132.76, 156.35, 161.60, 172.57; HRMS (EI) m/z calcd for C$_{11}$H$_{13}$NO$_4$ (M$^+$) 223.0845, found 223.0851; LRMS (EI) m/z 224(M+H, 32), 195(21), 163(43), 153(100), 91(40), 77(19), 55(24); $[α]_D^{23}$=+35.0 (c=0.08, MeOH).

Example 19

1-[3-(tert-Butyldimethylsilanyloxymethyl)-2-methoxy-6-(trimethylsilanyl)pyridin-4-yl]propan-1-one To a solution of 2a (2.2 g, 6.5 mmol) and imidazole (1.1 g, 16 mmol) in DMF (3.2 mL) at 0° C. was added tert-butyldimethylsilylchloride (1.34 g, 8.9 mmol). The mixture was then heated at 35° C. After heating for 30 h, the reaction mixture was quenched with water and then extracted with hexane. The combined organic layers were washed with brine, dried over MgSO$_4$ and concentrated under reduced pressure to give 3.19 g of the crude product (100% yield) as a clear oil. The crude product was sufficiently pure for the subsequent reaction: $^1$H NMR (300 MHz, CDCl$_3$) δ0.15 (s, 6H), 0.31 (s, 9H), 0.99 (s, 9H), 3.97 (s, 3H), 4.8 (s, 2H), 7.52 (s, 1H).

To a solution of the crude product (3.19 g, 6.5 mmol) in THF (25 mL) at −40° C. was added dropwise $^i$PrMgCl (7.0 mL, 2.0 M in THF). The mixture was stirred at −40° C. for 1 h, and then CuCN.2LiCl [prepared from CuCN (1.2 g, 13.4 mmol) and LiCl (1.16 g, 27.4 mmol)] in THF (30 mL)] was added. After 15 min propionyl chloride (2.7 mL, 31.5 mmol) was added, then the reaction mixture was stirred 1 h at −40° C. and 15 min at rt. The reaction was quenched with brine and extracted with Et$_2$O. The combined organic layers were washed with brine, dried over MgSO$_4$ and concentrated under reduced pressure. The residue was purified by flash chromatography (gradient hexane to hexane/Et$_2$O 95:5) to afford 7 (2.04 g, 82%) as a yellowish oil. $^1$H NMR (300 MHz, CDCl$_3$) δ0.09 (s, 6H), 0.29 (s, 9H), 0.91 (s, 9H), 1.18 (t, J=7.1 Hz, 3H), 2.85 (q, J=7.1 Hz, 2H), 3.99 (s, 3H), 4.78 (s, 2H), 6.9 (s, 1H); $^{13}$C NMR (75 MHz, CDCl$_3$) δ−1.95, 7.69, 18.59, 25.95, 36.52, 53.36, 57.62, 118.35, 118.97, 148.31, 160.23, 164.4, 207.17; IR (film, NaCl, cm$^{-1}$) 840.7, 1076.6, 1343.5, 1455.2, 1715.8, 2957.1; LRMS (70 eV, EI) m/z (rel int %) 324, (M$^+$−$^t$Bu) 256, 192, 160, 128, 96, 64 (100). HRMS m/z calcd for C$_{15}$H$_{26}$NO$_3$Si$_2$ (M$^+$−$^t$Bu) 324.1451, found 324.1452.

Example 20

1-[2-Methoxy-3-methoxymethoxymethyl-6-(trimethylsilanyl)pyridin-4-yl]propan-1-one (18)

Treatment of 2a (4.0 g, 10.5 mmol) according to the procedure in the second part of Example 19 afforded 18 (2.2 g, 69%) as a yellowish oil, after purification of the crude residue by flash chromatography (gradient hexane to hexane/EtOAc 10:1): $^1$H NMR (300 MHz, CDCl$_3$) δ0.28 (s, 9H), 1.98 (t, J=7.1 Hz, 3H), 2.82 (q, J=7.1 Hz, 2H), 3.37 (s, 3H), 3.99 (s, 3H), 4.62 (s, 2H), 4.64 (s, 2H), 6.94 (s, 1H); $^{13}$C NMR (75 MHz, CDCl$_3$) δ−5.6, −2.0, 7.7, 36.4, 53.5, 61.1, 96.4, 115.2, 118.4, 148.5, 161.1, 165.5, 206.8; IR (film, NaCl, cm$^{-1}$) 2951, 1708, 1451, 1342, 1046, 839; LRMS (70 eV, EI) m/z (rel int %) 296 (M$^+$−15), 266 (100), 248, 234, 100, 89, 73, 59; HRMS m/z calcd for C$_{14}$H$_{22}$NO$_4$Si (M$^+$−CH$_3$) 296.1318, found 296.1313.

Example 21

(E)-3-[2-Methoxy-3-methoxymethoxymethyl-6-(trimethylsilanyl)pyridin-4-yl]pent-2-enoic acid methyl ester (19E/Z)

To a mixture of trimethyl phosphonoacetate (2.5 mL, 15.3 mmol) and $^t$BuOK (1.7 g, 15.3 mmol) in THF (20 mL) at 0° C. (1 h) was added a THF (10 nmL) solution of 18 (1.2 g, 3.7 mmol). The mixture was stirred at reflux for 36 h. Purification of the crude residue by flash chromatography (hexane/EtOAc 92:8) followed by preparative HPLC (hexane/EtOAc 92:8, Novapak normal phase cartridge column, 10 mL/min), afforded in order of elution; 18 (123.3 mg, 10%), 19E (387.0 mg, 27%) and 19Z (609.3 mg, 43%) as clear oils: 19E; $^1$H NMR (300 MHz, CDCl$_3$) δ0.28 (s, 9H), 0.99 (t, J=7.6 Hz, 3H), 2.99 (q, J=7.6 Hz, 2H), 3.42 (s, 3H), 3.75 (s, 3H), 4.02 (s, 3H), 4.47 (s, 2H), 4.72 (s, 2H), 5.8 (s, 1H), 6.84 (s, 1H); $^{13}$C NMR (75 MHz, CDCl$_3$) δ−2.0, 12.3, 14.2, 26.6, 51.2, 53.4, 55.3, 61.9, 96.7, 115.4, 118.9, 121.1, 150.9, 160.3, 162.2, 164.9, 166.2; IR (film, NaCl, cm$^{-1}$) 2949, 1723, 1341, 1042, 840; LRMS (70 eV, EI) m/z (rel int %) 367 (M$^+$), 352, 322, 308 (100), 290, 276, 246, 232, 99, 57; HRMS m/z calcd for C$_{18}$H$_{29}$NO$_5$Si (M$^+$) 367.1815,m found 367.1802. 19Z: $^1$H NMR (300 MHz, CDCl$_3$) δ0.26 (s, 9H), 1.11 (t, J=7.2 Hz, 3H), 2.38–2.48 (m, 2H), 3.4 (s, 3H), 3.53 (s, 3H), 3.99 (s, 3H), 4.35 (d, J=10.2 Hz, 1H), 4.51 (d, J=10.2 Hz, 1H), 4.66 (dd, J=6.3 and 14.2 Hz, 2H), 5.94 (s, 1H), 6.72 (s, 1H); $^{13}$C NMR (75 MHz, CDCl$_3$ δ−1.9, 11.4, 33.1, 51.1, 53.2, 55.2, 61.9, 96.5, 114.5, 116.3, 120.6, 150.0, 159.0, 161.7, 164.3, 165.6; IR (film, NaCl, cm$^{-1}$) 2941, 1732, 1559, 1457, 1342, 1054, 836; LRMS (70 eV, EI) m/z (rel int %) 367 (M$^+$), 322, 290, 278, 262, 139 (100), 89, 73; HRMS m/z calcd for C$_{18}$H$_{29}$NO$_5$Si (M$^+$) 367.1815, found 367.1820.

Example 22

5-Ethyl-1-methoxy-3-(trimethylsilanyl)-9H-8-oxa-2-aza-benzocyclohepten-7-one (20)

To a solution of rac-10a (92.5 mg, 0.3 mmol) in the THF (6 mL) at rt was added methoxycarbonylsulfamoyl triethylammonium hydroxide (Burgess reagent, 85.6 mg, 0.4 mmol). After stirring for 12 h, the reaction mixture was concentrated under reduced pressure and the residue purified by flash chromatography (hexane/EtOAc 87:13) to afford 42 (72.0 mg, 83% yield) as a clear oil: $^1$H NMR (300 MHz, CDCl$_3$) δ0.31 (s, 9H), 1.16 (t, J=7.4 Hz, 3H), 2.68 (q, J=7.4 Hz, 2H), 4.01 (s, 3H), 6.37 (s, 1H), 7.11 (s, 1H); $^{13}$C NMR (75 MHz, CDCl$_3$) δ –2.2, 6.9, 19.9, 53.4, 60.4, 116.1, 118.4, 121.4, 144.9, 151.4, 160.2, 166.9, 167.8; IR (film NaCl, cm$^{-1}$) 2964, 1723, 1550, 1451, 1345, 838; LRMS (70 eV, EI) m/z (rel int %) 291 (M$^+$), 276, 262, (100), 248, 232, 89, 73, 59; HRMS m/z calcd for C$_{15}$H$_{21}$NO$_3$Si (M$^+$) 291.1291, found 291.1282.

Example 23

(5RS, 6SR)-5-Ethyl-5,6-dihydroxy-1-methoxy-3-(trimethylsilanyl)-5,9-dihydro-6H-8-oxz-2-aza-benzocyclohepten-7-one (rac-21)

To a stirred solution of potassium ferricyanide (102.0 mg, 0.3 mmol), potassium carbonate (43 mg, 0.31 mmol), methanesulfonamide (10.0 mg, 0.1 mmol), DABCO (1.0 mg, 7.2 μmol, 7.5 mol %) and OS$_4$ (6.0 μL of a 2.5 wt. % in $^t$BuOH, 5.0 mol %) in 1:1 $^t$BuOH/H$_2$O (1 mL) at 0° C. was added 20 (30 mg, 0.1 mmol). The mixture was stirred for 24 h, and then potassium osmate dihydrate (8.0 mg, 22.0 μmol, 20.0 mol %) and more DABCO (4.0 mg, 28.0 μmol, 30.0 mol %) were added. The cooling bath was removed and the mixture was allowed to warm to rt. After 24 h, the reaction was quenched with Na$_2$SO$_3$ (10.0 mg) and stirred for 30 min. The mixture was diluted with CH$_2$Cl$_2$ and washed with brine. The aqueous layer was extracted three times with CH$_2$Cl$_2$. The combined organic extracts were dried over MgSO$_4$ and concentrated under reduced pressure. The crude product was purified by flash chromatography (gradient hexane to hexane/EtOAc 75:25) to give, in order of elution, starting material 20 (9.1 mg, 30%) and desired product 21 (11.3 mg, 34% as clear oil: $^1$H NMR (300 MHz, CDCl$_3$) δ0.3 (s, 9H), 0.74 (t, J=7.3 Hz, 3H), 1.8–1.94 (m, 1H), 2.18–2.32 (m, 1H), 2.92 (bs, 1H), 3.82 (bs, 1H), 4.0 (s, 3H), 5.04 (d, J=14.6 Hz, 1H), 5.71 (d, J=14.6 Hz, 1H), 7.37 (s, 1H); $^{13}$C NMR (125 MHz, CDC$_3$) δ –1.8, 9.0, 34.9, 54.2, 61.3, 69.1, 77.10, 114.9, 121.8, 149.5, 159.7, 166.4, 174.1; IR (film, NaCl, cm$^{-1}$) 3409, 2947, 1748, 1346, 836; LRMS (70eV, EI) m/z (rel int %) 325 (M$^+$), 310, 296, 250 (100), 236, 89, 73; HRMS m/z calcd for C$_{15}$H$_{23}$NO$_5$Si (M$^+$) 325.1345, found 325.1343.

Example 24

(5R, 6S)-5-Ethyl-5,6-dihydroxy-1-methoxy-3-(trimethylsilanyl)(-5,9-dihydro-6H-8-oxa-2-aza-benzocyclohepten-7-one ((+)-21)

To a stirred solution of potassium ferricyanide (102.0 mg, 0.3 mmol), potassium carbonate (43.0 mg, 0.3 mmol), methanesulfonamide (10.0 mg, 0.1 mmol), (DHQD)$_2$-PYR (6.8 mg, 7.0 μmol, 7.5 mol %) and OsO$_4$ (65.0 μL of a 2.5 wt. % in $^t$BuOH, 5.0 mol %) in 1:1 $^t$BuOH/H$_2$O (1 mL) at 0° C. was added 20 (30.0 mg, 0.1 mmol). The mixture was stirred for 24 h, and then potassium osmate dihydrate (4.0 mg, 121.0 μmol, 10.0 mol %) was added. After 48 h, the reaction was quenched with Na$_2$SO$_3$ (10.0 mg) and stirred for 30 min. The mixture was diluted with CH$_2$Cl$_2$ and washed with brine. The aqueous layer was extracted three times with CH$_2$Cl$_2$. The combined organic extracts were dried over MgSO$_4$ and concentrated under reduced pressure. The crude product was purified by flash chromatography (gradient hexane to hexane/EtOAc 80:20) to give (+)-21 (16.1 mg, 48%) as a clear oil. Lactone 21 was analyzed for enantiomeric purity by using a Chiralcel-OD column with 95:5 hexane:$^i$PrOH as the eluent (1 mL/min), and the racemate rac-21 as the standard. The enantiomeric excess was shown to be 67% [(5R, 6S) major, Rt 17.3 min; (5S, 6R) minor, Rt 20.3 min]: [α]$^{23}_D$=+112 (c=1.07, MeOH).

Although the present invention has been described in detail in connection with the above examples, it is to be understood that such detail is solely for that purpose and that variations can be made by those skilled in the art without departing from the spirit of the invention except as it may be limited by the following claims.

What we claim is:

1. A compound having the formula:

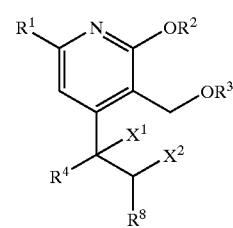

III wherein R$^1$ is fluorine, chlorine or SiR$^5$R$^6$R$^7$, wherein R$^5$, R$^6$, and R$^7$ are independently the same or different an alkyl group or an aryl group, R$^2$ is an alkyl group, R$^3$ is a protecting group, R$^4$ is an alkyl group, an allyl group, a propargyl group or a beuzyl group, R$^8$ is —CHO, —CH$_2$OH, —CH$_2$OR$^9$, wherein R$^9$ is a protecting group, —CO$_2$H, or —CO$_2$R$^{10}$ wherein R$^{10}$, is an alkyl group or an aryl group, and X$^1$ is OH, X$^2$ is H or OH, or X$^1$ and X$^2$ together are O, OS(O)O or OS(O$_2$)O.

2. The compound of claim 1 wherein R$^3$ is an acetate group, a methoxymethyl group or a tert-butyldimethylsilyl group.

3. The compound of claim 1 wherein R$^{10}$ is a lower alkyl group.

4. The compound of claim 1 wherein R$^1$ is a trimethylsilyl group, R$^2$ is a lower alkyl group, R$^3$ is a methoxymethyl group, R$^4$ is an ethyl group, R$^8$ is CH$_2$OH, CHO, CO$_2$Me or CO$_2$Et, X$^1$ is OH, and X$^2$is H or X$^1$ and X$^2$ together are O.

5. A compound having the formula:

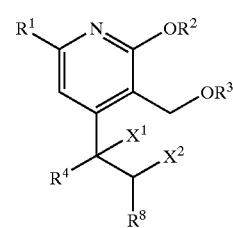

III wherein R$^1$ is hydrogen, fluorine, chlorine or SiR$^5$R$^6$R$^7$, wherein R$^5$, R$^6$, and R$^7$ are independently the same or different an alkyl group or an aryl group, R$^2$ is an alkyl group, R$^3$ is a protecting group, R$^4$ is an alkyl group, an allyl group, a propargyl group or a benzyl group, R$^8$ is —CHO, —CH$_2$OH, —CH$_2$OR$^9$, wherein R$^9$ is a protecting group, or —CO$_2$H, and X$^1$ is OH, X$^2$ is OH, or X$^1$ and X$^2$ together are O, OS(O)O or OS(O$_2$)O.

6. The compound of claim 5 wherein R$^3$ is an acetate group, a methoxymethyl group or a tert-butyldimethylsilyl group.

7. The compound of claim 5 wherein $R^{10}$ is a lower alkyl group.

8. The compound of claim 5 wherein $R^1$ is H or a trimethylsilyl group, $R^2$ is a lower alkyl group, $R^3$ is a methoxymethyl group, $R^4$ is an ethyl group, $R^8$ is $CH_2OH$, CHO, $CO_2Me$ or $CO_2Et$, and $X^1$ is OH, $X^2$ is OH or $X^1$ and $X^2$ together are O.

9. A compound having the formula:

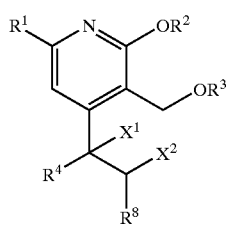

wherein $R^1$ is hydrogen, fluorine, chlorine or $SiR^5R^6R^7$, wherein $R^5$, $R^6$, and $R^7$ are independently the same or different an alkyl group or an aryl group, $R^2$ is an alkyl group, $R^3$ is a protecting group, $R^4$ is an alkyl group, an allyl group, a propargyl group or a benzyl group, $R^8$ is —CHO, —$CH_2OH$, —$CH_2OR^9$, wherein $R^9$ is a protecting group, and $X^1$ is OH, $X^2$ is H or OH, or $X_1$ and $X^2$ together are O, OS(O)O or OS(O$_2$)O.

10. The compound of claim 9 wherein $R^3$ is an acetate group, a methoxymethyl group or a tert-butyldimethylsilyl group.

11. The compound of claim 9 wherein $R^1$ is a trimethylsilyl group, $R^2$ is a lower alkyl group, $R^3$ is a methoxymethyl group, $R^4$ is an ethyl group, $R^8$ is $CH_2OH$ or CHO, $X^1$ is OH, and $X^2$ is H or $X^1$ and $X^2$ together are O.

12. A method of synthesizing a compound having the formula:

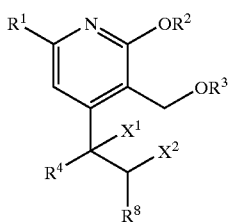

wherein $R^1$ is hydrogen, fluorine, chlorine or $SiR^5R^6R^7$, wherein $R^5$, $R^6$, and $R^7$ are independently the same or different an alkyl group or an aryl group, $R^2$ is an alkyl group, $R^3$ is a protecting group, $R^4$ is an alkyl group, an allyl group, a propargyl group or a benzyl group, $R^8$ is —CHO, —$CH_2OH$, —$CH_2OR^9$, wherein $R^9$ is a protecting group, —$CO_2H$, or —$CO_2R^{10}$, wherein $R^{10}$ is an alkyl group or an aryl group, and $X^1$ is OH, $X^2$ is H or OH, or $X^1$ and $X^2$ together are O, from a compound having the formula:

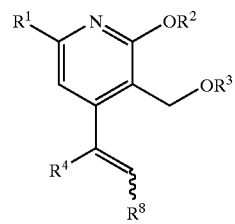

comprising the step of asymmetrically hydroxylating compound (II) or asymmetrically epoxidating compound (II).

13. The method of claim 12 wherein $X^1$ and $X^2$ together are O and asymmetric epoxidation is effected by Sharpless asymmetric epoxidation, Jacobsen asymmetric epoxidation or Jacobsen-Katsuki asymmetric epoxidation.

14. The method of claim 12 wherein Sharpless asymmetric epoxidation is effected and $R^8$ is (E)—$CH_2OH$.

15. The method of claim 12 wherein asymmetric dihydroxylation is effected and $X^1$ and $X^2$ are OH.

16. The method of claim 15 wherein Sharpless asymmetric dihydroxylation is effected.

17. The method of claim 15 further comprising the step of converting diols $X^1$ and $X^2$ to cyclic sulfites by a sulfinylation reagent.

18. The method of claim 17 wherein the sulfinylation reagent is $SOCl_2$.

19. The method of claim 15 further comprising the step of converting diols $X^1$ and $X^2$ to cyclic sufates by a sulfonylating reagent.

20. The method of claim 19 wherein the sulfonylating agent is $SO_2Cl_2$.

21. A method of synthesizing a compound having the formula:

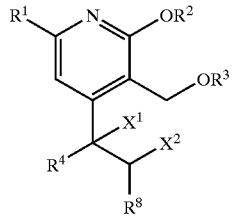

wherein $R^1$ is hydrogen, fluorine, chlorine or $SiR^5R^6R^7$, wherein $R^5$, $R^6$, and $R^7$ are independently the same or different an alkyl group or an aryl group, $R^2$ is an alkyl group, $R^3$ is a protecting group, $R^4$ is an alkyl group, an allyl group, a propargyl group or a benzyl group, $R^8$ is —CHO, —$CH_2OH$, —$CH_2OR^9$, wherein $R^9$ is a protecting group —$CO_2H$, or —$CO_2R^{10}$, wherein $R^{10}$ is an alkyl group or an aryl group, and $X^1$ is OH, $X^2$ is H or OH, or $X^1$ and $X^2$ together are O, OS(O)O or OS(O$_2$)O, comprising the steps of:

a) converting the ketone of the compound:

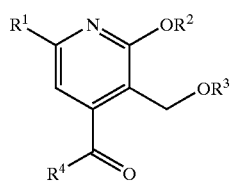

I to an alkene to synthesize a compound having the formula:

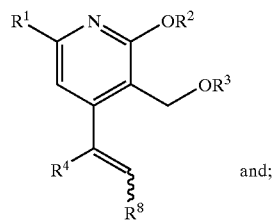

II and;

b) asymmetrically hydroxylating compound (II) or asymmetrically epoxidating compound (II).

22. The method of claim 21 wherein the dehydrating agent is methoxycarbonylsulfamoyltriethylammonium hydroxide.

23. A compound having the formula:

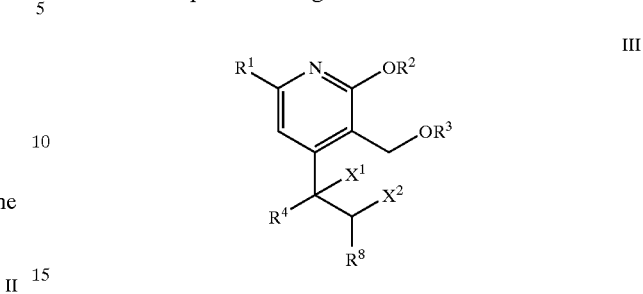

III wherein $R^1$ is $SiR^5R^6R^7$, wherein $R^5$, $R^6$, and $R^7$ are independently the same or different an alkyl group or an aryl group, $R^2$ is an alkyl group, $R^3$ is a protecting group, $R^4$ is an alkyl group, an allyl group, a propargyl group or a benzyl group, $R^8$ is —CHO, —CH$_2$OH, —CH$_2$OR$^9$, wherein $R^9$ is a protecting group, —CO$_2$H, or —CO$_2$R$^{10}$ wherein $R^{10}$, is an alkyl group or an aryl group, and $X^1$ is OH, $X^2$ is H or OH, or $X^1$ and $X^2$ together are O, OS(O)O or OS(O$_2$)O.

* * * * *